(12) United States Patent
Dooley et al.

(10) Patent No.: US 6,350,430 B1
(45) Date of Patent: Feb. 26, 2002

(54) MELANOCORTIN RECEPTOR LIGANDS AND METHODS OF USING SAME

(75) Inventors: Colette T. Dooley; Beverly E. Girten, both of San Diego; Richard A. Houghten, Del Mar, all of CA (US)

(73) Assignee: Lion Bioscience Science AG (DE)

( * ) Notice: Subject to any disclaimer, the term of this patent is extended or adjusted under 35 U.S.C. 154(b) by 0 days.

(21) Appl. No.: 09/027,108

(22) Filed: Feb. 20, 1998

Related U.S. Application Data

(60) Provisional application No. 60/063,622, filed on Oct. 27, 1997.

(51) Int. Cl.[7] .................................................. A61K 51/00

(52) U.S. Cl. ...................... 424/1.11; 530/312; 530/329; 514/17; 435/7.21

(58) Field of Search ................................. 530/329, 312; 514/17; 930/217; 424/1.11; 435/7.21

(56) References Cited

U.S. PATENT DOCUMENTS

| | | |
|---|---|---|
| 5,010,175 A | 4/1991 | Rutter et al. ................. 530/334 |
| 5,420,109 A | 5/1995 | Suto et al. ..................... 514/8 |
| 5,618,791 A | 4/1997 | Du ............................... 514/17 |
| 5,726,156 A | 3/1998 | Girten et al. ................. 514/16 |
| 5,731,408 A * | 3/1998 | Hadley et al. ............... 530/312 |

FOREIGN PATENT DOCUMENTS

| | | |
|---|---|---|
| WO | WO91/19735 | 12/1991 |
| WO | WO95/13086 | 5/1995 |
| WO | WO96/27386 | 9/1996 |
| WO | WO97/22356 | 6/1997 |

OTHER PUBLICATIONS

Berge et al., "Pharmaceutical Salts," *J. Pharm. Sci.*, 66:1–19 (1977).
Catania and Lipton, "α–Melanocyte–Stimulating Hormone Peptides in Host Responses," *Annals N.Y. Acad. Sci.*, 680:412–423 (1993).
Catania et al., "The Neuropeptide α–MSH Has Specific Receptors on Neutrophils and Reduces Chemotaxis In Vitro," *Peptides*, 17(4):675–679 (1996).
Dorr et al., "Evaluation of melanotan–II, a superpotent cyclic melanotropic peptide in a pilot phase–I clinical study," *Life Sciences*, 58:1777–1784 (1996).
Fan et al., "Role of melanocorintergic neurons in feeding and the agouti obesity syndrome," *Nature*, 385:165–168 (1997).
Friedman, "The alphabet of weight control," *Nature*, 385:119–120 (1997).
Gallop et al., "Applications of combinatorial technologies to drug discovery. 1. Background and peptide combinatorial libraries," *J. Med. Chem.*, 37:1233–1251 (1994).
Gura, "Obesity Sheds Its Secrets," *Science*, 275:751–753 (1997).
Hotamisligil and Spiegelman, "Tumor Necrosis Factor α: A Key Component of the Obesity–Diabetes Link," *Diabetes*, 43:1271–1278 (1994).
Hotamisligil et al., "Reduced tyrosine kinase activity of the insulin receptor in obesity–diabetes. Central role of tumor necrosis factor–alpha," *J. Clin. Invest.*, 94:1543–1549 (1994).
Hotamisligil et al., "Increased adipose tissue expression of tumor necrosis factor–alpha in human obesity and insulin resistance," *J. Clin. Invest.*, 95:2409–2415 (1995).
Huszar et al., "Targeted Disruption of the Melanocortin–4 Receptor Results in Obesity in Mice," *Cell*, 88:131–141 (1997).
Ollmann et al., "Antagonism of Central Melanocortin Receptors in Vitro and in Vivo by Agouti–Related Protein," *Science*, 278:135–137 (1997).
Platzer et al., "Up–regulation of monocytic IL–10 by tumor necrosis factor–α and cAMP elevating drugs," *International Immunology*, 7(4):517–523 (1995).
Star et al., "Evidence of autocrine modulation of macrophage nitric oxide synthase by α–melanocyte–stimulating hormone," *Proc. Natl. Acad. Sci. USA*, 92:8016–8020 (1995).
Tatro, "Receptor biology of the melanocortins, a family of neuroimmunomodulatory peptides," *Neuroimmunomodulation*, 3:259–284 (1996).
Xia et al., "Expression of melanocortin 1 receptor in periaqueductal gray matter," *Neuroreport*, 6:2193–2196 (1995).
Abou–Mohamed et al., "HP–228, a novel synthetic peptide, inhibits the induction of nitric oxide synthase in vivo but not in vitro," *J. Pharmacology and Experimental* 275:584–591 (1995).
Chowdhary et al., "Localization of the human melanocortin–5 receptor gene (MC5R) to chromosome band 18p11.2 by fluorescence in situ hybridization," *Cytogenet Cell Genet* 68:79–81 (1995).
Dooley et al., "Melanocortin receptor binding assay in rat brain homogenate: identification of tetrapeptide ligands from a combinatorial library," *Society for Neuroscience* 23:964 Abstract 383.18 (Aug. 21, 1997).
Frandberg et al., "Glutamine$^{235}$ and arginine$^{272}$ in human melanocortin 5 receptor determines its low affinity to MSH," *Biochem. Biophys. Res. Commun.* 236:489–492 (1997).

(List continued on next page.)

*Primary Examiner*—F. T. Moezie
(74) *Attorney, Agent, or Firm*—Campbell & Flores LLP

(57) ABSTRACT

The invention provides ligands for melanocortin receptors. For example, the invention provides the melanocortin receptor peptide ligand Ac-Nlc-Gln-His-(p(I)-D-Phe)-Arg-(D-Trp)-Cly-NH$_2$, (SEQ ID NO: 1), where the iodo group is unlabeled or radioactively labeled. The invention additionally provides methods of assaying for melanocortin receptors in a cell or tissue such as brain. The invention also relates to pharmaceutical compositions comprising a pharmaceutically acceptable carrier and a melanocortin receptor ligand and to methods of administering the pharmaceutical composition to a subject. The invention further provides tetrapeptide ligands for melanocortin receptors and methods of altering melanocortin receptor activity.

5 Claims, 12 Drawing Sheets

OTHER PUBLICATIONS

Gantz et al., "Molecular cloning, expression, and gene localization of a fourth melancortin receptor," *J. Biol. Chem.* 268:15174–15179 (1993).

Gantz et al., "Molecular cloning of a novel melanocortin receptor," *J. Biol. Chem.* 268:8246–8250 (1993).

Gantz et al., "Molecular cloning, expression, and characterization of a fifth melanocortin receptor," *Biochem. Biophys. Res. Commun.* 200:1214–1220 (1994).

Haskell–Luevano et al., "Binding and cAMP studies of melanotropin peptides with the cloned human peripheral melanocortin receptor, hMC1R," *Biochem. Biophys. Res. Commun.* 204:1137–1142 (1994).

Haskell–Luevano et al., "Discovery of Prototype peptidomimetic agonists at the human melanocortin receptors MC1R and MC4R," *J. Med. Chem.* 40:2133–2139 (1997).

Schiöth et al., "Characterization of the binding of MSH–B, HP–228, GHRP–6 and 153N–6 to the human melanocortin receptor subtypes," *Neuropeptides* 31:565–571 (1997).

* cited by examiner

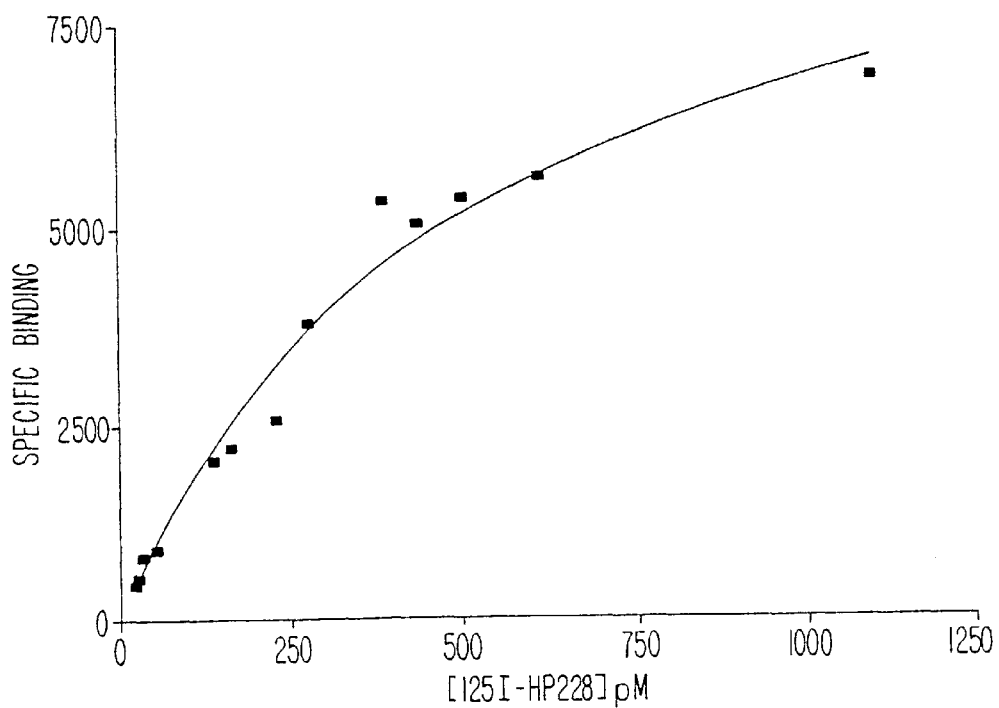
FIG. IA
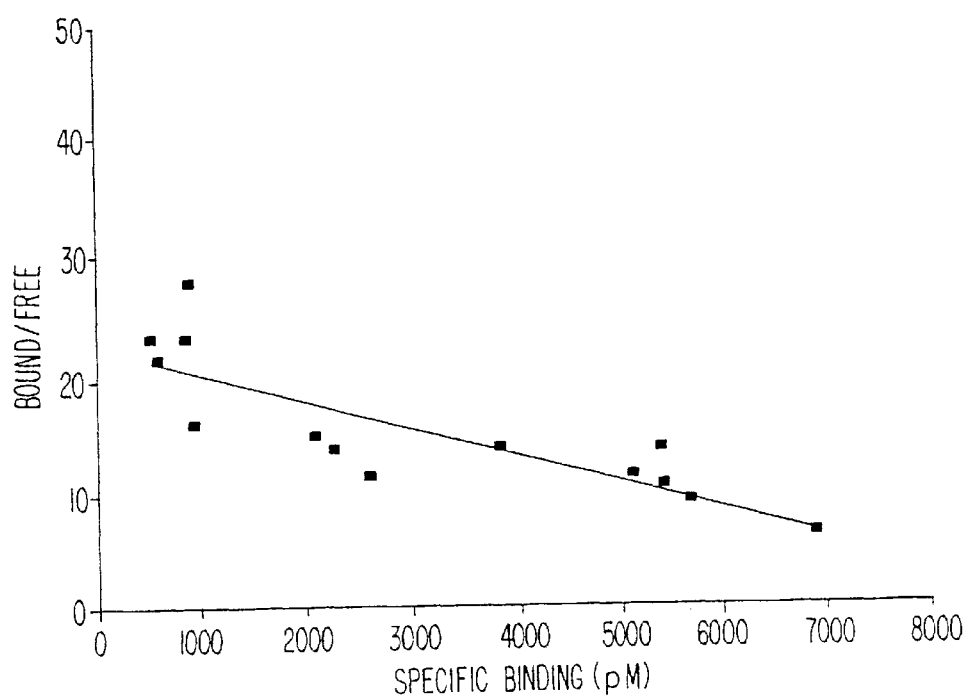
FIG. IB

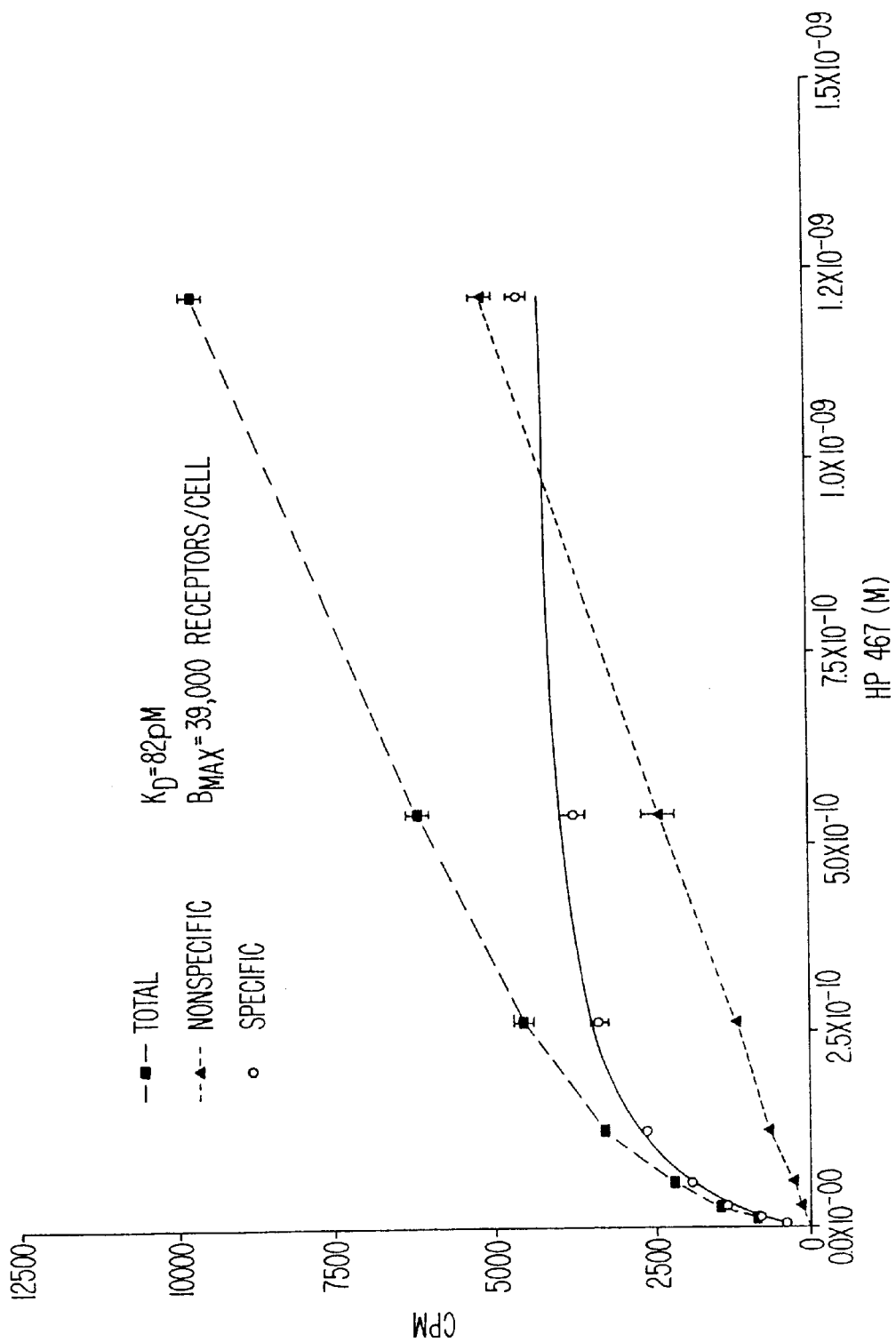

SEQUENCE LISTING

<160> NUMBER OF SEQ ID NOS: 18

<210> SEQ ID NO 1
<211> LENGTH: 7
<212> TYPE: PRT
<213> ORGANISM: Artificial Sequence
<220> FEATURE:
<221> NAME/KEY: MOD_RES
<222> LOCATION: (1)
<223> OTHER INFORMATION: Nle
<221> NAME/KEY: MOD_RES
<222> LOCATION: (1)
<223> OTHER INFORMATION: ACETYLATION;
<221> NAME/KEY: MOD_RES
<222> LOCATION: (7)
<223> OTHER INFORMATION: AMIDATION
<221> NAME/KEY: SITE
<222> LOCATION: (4)
<223> OTHER INFORMATION: Xaa is Phe in the D-Configuration.
<221> NAME/KEY: SITE
<222> LOCATION: (6)
<223> OTHER INFORMATION: Xaa is Trp in the D-Configuration
<221> NAME/KEY: MOD_RES
<222> LOCATION: (4)
<223> OTHER INFORMATION: Xaa is para-iodinated.
<223> OTHER INFORMATION: Description of Artificial Sequence: Synthetic
      Construct

<400> SEQUENCE: 1

Xaa Gln His Xaa Arg Xaa Gly
 1               5

<210> SEQ ID NO 2
<211> LENGTH: 13
<212> TYPE: PRT
<213> ORGANISM: Homo sapiens
<220> FEATURE:
<221> NAME/KEY: MOD_RES
<222> LOCATION: (1)
<223> OTHER INFORMATION: ACETYLATION
<221> NAME/KEY: MOD_RES
<222> LOCATION: (13)
<223> OTHER INFORMATION: AMIDATION

<400> SEQUENCE: 2

Ser Tyr Ser Met Glu His Phe Arg Trp Gly Lys Pro Val
 1               5                  10

<210> SEQ ID NO 3
<211> LENGTH: 13
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<221> NAME/KEY: MOD_RES
<222> LOCATION: (4)
<223> OTHER INFORMATION: Nle
<221> NAME/KEY: SITE
<222> LOCATION: (7)
<223> OTHER INFORMATION: Xaa is Phe in the D-Configuration.
<221> NAME/KEY: MOD_RES
<222> LOCATION: (13)
<223> OTHER INFORMATION: AMIDATION
<223> OTHER INFORMATION: Description of Artificial Sequence: Synthetic
      Construct

<400> SEQUENCE: 3

Ser Tyr Ser Xaa Glu His Xaa Arg Trp Gly Lys Pro Val
 1               5                  10

```
<210> SEQ ID NO 4
<211> LENGTH: 11
<212> TYPE: PRT
<213> ORGANISM: Homo sapiens

<400> SEQUENCE: 4

Tyr Val Met Gly His Phe Arg Trp Asp Arg Phe
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      Construct

<400> SEQUENCE: 5

Tyr Val Met Gly His Phe Arg Trp Asp Arg Phe Gly
1               5                   10

<210> SEQ ID NO 6
<211> LENGTH: 27
<212> TYPE: PRT
<213> ORGANISM: Homo sapiens

<400> SEQUENCE: 6

Tyr Val Met Gly His Phe Arg Trp Asp Arg Phe Gly Arg Arg Asn Gly
1               5                   10                  15

Ser Ser Ser Ser Gly Val Gly Gly Ala Ala Gln
            20                  25

<210> SEQ ID NO 7
<211> LENGTH: 7
<212> TYPE: PRT
<213> ORGANISM: Homo sapiens

<400> SEQUENCE: 7

Met Glu His Phe Arg Trp Gly
1               5

<210> SEQ ID NO 8
<211> LENGTH: 22
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 8

Ala Glu Lys Lys Asp Glu Gly Pro Tyr Arg Met Glu His Phe Arg Trp
1               5                   10                  15

Gly Ser Pro Pro Lys Glu
            20

<210> SEQ ID NO 9
<211> LENGTH: 7
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<221> NAME/KEY: MOD_RES
<222> LOCATION: (1)
```

```
<223> OTHER INFORMATION: Nle
<221> NAME/KEY: SITE
<222> LOCATION: (4)
<223> OTHER INFORMATION: Xaa is Phe in the D-configuration
<221> NAME/KEY: SITE
<222> LOCATION: (6)
<223> OTHER INFORMATION: Xaa is Trp in the D-Configuration
<221> NAME/KEY: MOD_RES
<222> LOCATION: (7)
<223> OTHER INFORMATION: AMIDATION
<223> OTHER INFORMATION: Description of Artificial Sequence: Synthetic
      Construct

<400> SEQUENCE: 9

Xaa Gln His Xaa Arg Xaa Gly
  1               5

<210> SEQ ID NO 10
<211> LENGTH: 4
<212> TYPE: PRT
<213> ORGANISM: Artificial Sequence
<220> FEATURE:
<221> NAME/KEY: SITE
<222> LOCATION: (2)
<223> OTHER INFORMATION: Xaa is D- 4-chlorophenylalanine; (pCL-f).
<221> NAME/KEY: SITE
<222> LOCATION: (4)
<223> OTHER INFORMATION: Xaa is naphthylalanine in the D-configuration;
      (D-Nal).
<223> OTHER INFORMATION: Description of Artificial Sequence: Synthetic
      Construct

<400> SEQUENCE: 10

His Xaa Arg Xaa
1

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide
<221> NAME/KEY: MOD_RES
<222> LOCATION: (2)
<223> OTHER INFORMATION: Xaa is D-4-chlorophenylalanine; (pCl-f).
<221> NAME/KEY: MOD_RES
<222> LOCATION: (3)
<223> OTHER INFORMATION: Xaa is cyclohexylalanine; (Cha).
<221> NAME/KEY: SITE
<222> LOCATION: (4)
<223> OTHER INFORMATION: Xaa is Arg in the D-Configuration.

<400> SEQUENCE: 11

His Xaa Xaa Xaa
1

<210> SEQ ID NO 12
<211> LENGTH: 4
<212> TYPE: PRT
<213> ORGANISM: Artificial Sequence
<220> FEATURE:
<221> NAME/KEY: MOD_RES
<222> LOCATION: (1)
<223> OTHER INFORMATION: Xaa is lysine (Alpha-Fmoc); (Alpha-FmLys).
<221> NAME/KEY: MOD_RES
<222> LOCATION: (2)
<223> OTHER INFORMATION: Xaa is D-4-chlorophenylalanine; (pCl-f).
<221> NAME/KEY: MOD_RES
<222> LOCATION: (4)
<223> OTHER INFORMATION: Xaa is naphthylalanine; (Nal).
<223> OTHER INFORMATION: Description of Artificial Sequence:Synthetic
      Peptide
```

```
<400> SEQUENCE: 12

Xaa Xaa Arg Xa
1

<210> SEQ ID NO 13
<211> LENGTH: 4
<212> TYPE: PRT
<213> ORGANISM: Artificial Sequence
<220> FEATURE:
<221> NAME/KEY: MOD_RES
<222> LOCATION: (1)
<223> OTHER INFORMATION: Xaa is lysine (Alpha-Fmoc); (Alpha FmLys).
<221> NAME/KEY: MOD_RES
<222> LOCATION: (3)
<223> OTHER INFORMATION: Xaa is cyclohexylanine; (L-Cha).
<221> NAME/KEY: MOD_RES
<222> LOCATION: (4)
<223> OTHER INFORMATION: Xaa is naphthylalanine; (Nal).
<223> OTHER INFORMATION: Description of Artificial Sequence:Synthetic
      Peptide

<400> SEQUENCE: 13

Xaa Arg Xaa Xaa
1

<210> SEQ ID NO 14
<211> LENGTH: 4
<212> TYPE: PRT
<213> ORGANISM: Artificial Sequence
<220> FEATURE:
<221> NAME/KEY: MOD_RES
<222> LOCATION: (1)
<223> OTHER INFORMATION: Xaa is lysine (Alpha-Fmoc); (AlphaFmLys).
<221> NAME/KEY: MOD_RES
<222> LOCATION: (3)
<223> OTHER INFORMATION: Xaa is cyclohexylalanine; (L-Cha).
<221> NAME/KEY: SITE
<222> LOCATION: (4)
<223> OTHER INFORMATION: Xaa is arginine in D-configuration; (D-Arg).
<223> OTHER INFORMATION: Description of Artificial Sequence:Synthetic
      Peptide

<400> SEQUENCE: 14

Xaa Arg Xaa Xaa
  1

<210> SEQ ID NO 15
<211> LENGTH: 4
<212> TYPE: PRT
<213> ORGANISM: Artificial Sequence
<220> FEATURE:
<221> NAME/KEY: MOD_RES
<222> LOCATION: (1)
<223> OTHER INFORMATION: Xaa is lysine (Alpha-Fmoc); (AlphaFmLys).
<221> NAME/KEY: SITE
<222> LOCATION: (2)
<223> OTHER INFORMATION: Xaa is (2-thienyl)alanine in the D
      configuration;(D-Thi).
<221> NAME/KEY: MOD_RES
<222> LOCATION: (4)
<223> OTHER INFORMATION: Xaa is naphthylalanine; (Nal).
<223> OTHER INFORMATION: Description of Artificial Sequence:Synthetic
      Peptide

<400> SEQUENCE: 15

Xaa Xaa Arg Xaa
  1

<210> SEQ ID NO 16
<211> LENGTH: 4
```

```
<212> TYPE: PRT
<213> ORGANISM: Artificial Sequence
<220> FEATURE:
<221> NAME/KEY: MOD_RES
<222> LOCATION: (1)
<223> OTHER INFORMATION: Xaa is lysine (Alpha-Fmoc); (AlphaFmLys).
<221> NAME/KEY: MOD_RES
<222> LOCATION: (4)
<223> OTHER INFORMATION: Xaa is naphthylalanine; (Nal).
<223> OTHER INFORMATION: Description of Artificial Sequence:Synthetic
      Peptide

<400> SEQUENCE: 16

Xaa Arg Arg Xaa
 1

<210> SEQ ID NO 17
<211> LENGTH: 4
<212> TYPE: PRT
<213> ORGANISM: Artificial Sequence
<220> FEATURE:
<221> NAME/KEY: MOD_RES
<222> LOCATION: (2)
<223> OTHER INFORMATION: Xaa is D-4-chlorophenylalanine; (pCl-f).
<221> NAME/KEY: MOD_RES
<222> LOCATION: (4)
<223> OTHER INFORMATION: Xaa is naphthylalanine in the D-configuration;
      (D-Nal).
<223> OTHER INFORMATION: Description of Artificial Sequence:Synthetic
      Peptide

<400> SEQUENCE: 17

His Xaa Arg Xaa
 1

<210> SEQ ID NO 18
<211> LENGTH: 4
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<221> NAME/KEY: MOD_RES
<222> LOCATION: (2)
<223> OTHER INFORMATION: Xaa is D-4-chlorophenylalanine; (pCl-f).
<221> NAME/KEY: MOD_RES
<222> LOCATION: (4)
<223> OTHER INFORMATION: AMIDATION
<221> NAME/KEY: MOD_RES
<222> LOCATION: (4)
<223> OTHER INFORMATION: Xaa is naphthylalanine in the D-configuration;
      (D-Nal).
<223> OTHER INFORMATION: Description of Artificial Sequence:Synthetic
      Peptide

<400> SEQUENCE: 18

His Xaa Arg Xaa
```

MELANOCORTIN RECEPTOR LIGANDS AND METHODS OF USING SAME

CROSS REFERENCE TO RELATED APPLICATIONS

This application claims the benefit of priority of U.S. Provisional Application No. 60/063,622, filed Oct. 27, 1997, the entire contents of which is incorporated herein by reference.

BACKGROUND OF THE INVENTION

1. Field of the Invention

The present invention relates generally to the fields of peptide chemistry and molecular pathology and more specifically to novel melanocortin receptor ligands.

2. Background Information

The melanocortin (MC) receptors are a group of cell surface proteins that mediate a variety of physiological effects, including regulation of adrenal gland function such as production of the glucocorticoid cortisol and aldosterone; control of melanocyte growth and pigment production; thermoregulation; immunomodulation; and analgesia. Five distinct MC receptors have been cloned and are expressed in a variety of tissues, including melanocytes, adrenal cortex, brain, gut, placenta, skeletal muscle, lung, spleen, thymus, bone marrow, pituitary, gonads and adipose tissue (Tatro, *Neuroimmunomodulation* 3:259–284 (1996)). Three MC receptors, MC1, MC3 and MC4, are expressed in brain tissue (Xia et al., *Neuroreport* 6:2193–2196 (1995)).

A variety of ligands termed melanocortins function as agonists that stimulate the activity of MC receptors. The melanocortins include melanocyte-stimulating hormones (MSH) such as α-MSH, β-MSH and γ-MSH, as well as adrenocorticotropic hormone (ACTH). Individual ligands can bind to multiple MC receptors with differing relative affinities. The variety of ligands and MC receptors with differential tissue-specific expression likely provides the molecular basis for the diverse physiological effects of melanocortins and MC receptors.

A particularly potent MC receptor ligand is an α-MSH analogue, NDP. NDP has been used extensively to characterize MC receptors because it is chemically and enzymatically stable and binds with high affinity to all identified MC receptors. Despite the availability of NDP, no binding assay has been reported for the detection of MC receptors in brain tissue even though MC receptor messenger RNA is expressed in brain. Detection of MC receptors in brain is of particular interest since brain MC receptors mediate some of the physiological effects of melanocortins, including the antipyretic effect observed with experimentally induced fever.

Due to the varied physiological activities of MC receptors, high affinity ligands of MC receptors would be valuable to analyze the presence of MC receptors in particular cells or tissues. In addition, high affinity ligands of MC receptors could be used to exploit the varied physiological responses of MC receptors by functioning as potential therapeutic agents or as lead compounds for the development of therapeutic agents.

Thus, there exists a need for ligands that bind to MC receptors with high affinity and methods for detecting the presence of MC receptors in a cell or tissue such as brain. The present invention satisfies this need and provides related advantages as well.

SUMMARY OF THE INVENTION

The invention provides ligands for melanocortin (MC) receptors. For example, the invention provides the MC receptor peptide ligand Ac-Nle-Gln-His-(p(I)-D-Phe)-Arg-(D-Trp)-Gly-$N_2$, (SEQ ID NO:1), where the iodo group is unlabeled or radioactively labeled. The invention additionally provides methods of assaying for MC receptors in a cell or tissue such as brain. The invention also relates to pharmaceutical compositions comprising a pharmaceutically acceptable carrier and a melanocortin receptor ligand and to methods of administering the pharmaceutical composition to a subject. The invention further provides tetrapeptide ligands for MC receptors and methods of altering MC receptor activity.

BRIEF DESCRIPTION OF THE DRAWINGS

FIG. 1 shows a saturation binding isotherm for $^{125}$I-HP 467 (Ac-Nle-Gln-His-(p(I)-D-Phe)-Arg-(D-Trp)-Gly-$NH_2$ (SEQ ID NO:1)).

FIG. 7 shows an HP 457 saturation binding curve of mouse L cells expressing melanocortin receptor 4 (MC4).

DETAILED DESCRIPTION OF THE INVENTION

Figure 2:
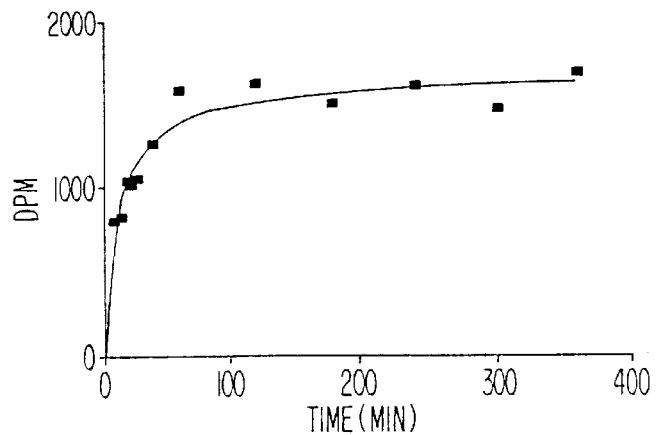
FIG. 2 shows the association rate for $^{125}$I-HP 467.
Figure 3:
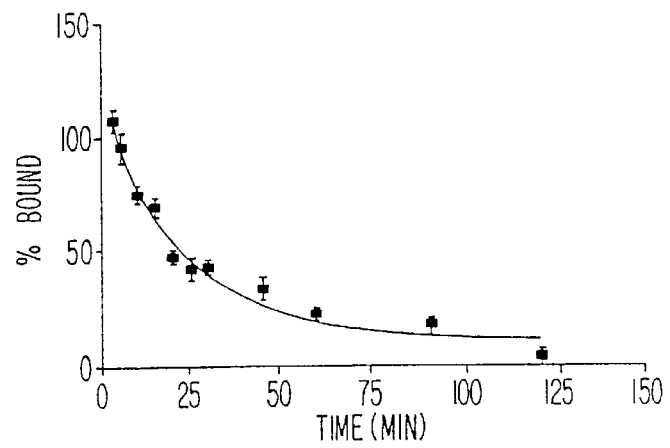
FIG. 3 shows the dissociation rate for $^{125}$I-HP 467.
Figure 4:
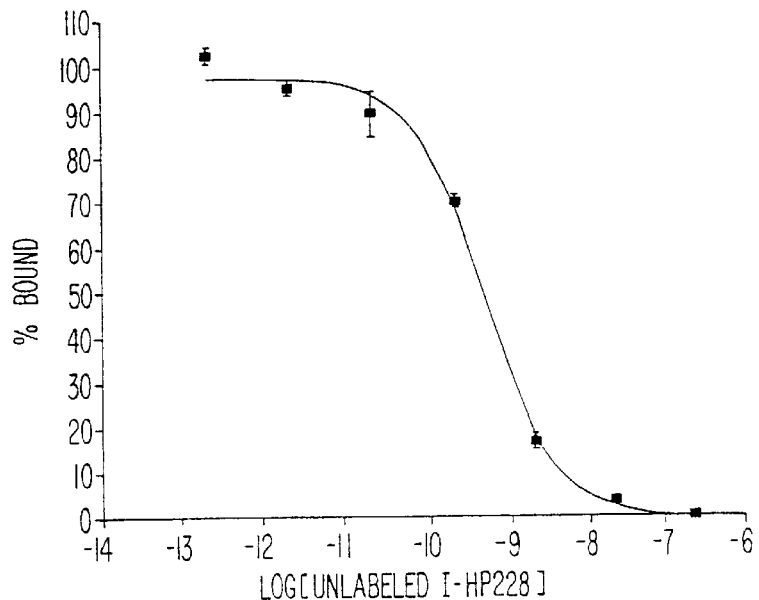
FIG. 4 shows a competition curve of unlabeled HP 467 for $^{125}$I-HP 467.

The invention provides ligands for MC receptors and methods for detecting the presence of MC receptors in a cell or tissue. For example, the invention provides the MC receptor peptide ligand HP 467, having the amino acid sequence Ac-Nle-Gln-His-(p(I)-D-Phe)-Arg-(D-Trp)-Gly-$NH_2$ (SEQ ID NO:1). HP 467 is a para-iodinated form of HP 228 Ac-(Nle)QHfRwG-$NH_2$ (SEQ ID NO:9) (see Table I), wherein the iodo group can be a stable nuclide such as $^{127}$I or an unstable nuclide, for example, radioactive $^{125}$I or $^{131}$I. HP 228 is a heptapeptide analogue of the α-melanocyte-stimulating hormone (α-MSH) analog having norleucine and D-phenylalanine (NDP) (Ac-SYS(Nle)EHfRWGKPV-$NH_2$; SEQ ID NO:3) (see Table I) and, like NDP, is both more potent and more stable than α-MSH. Table I shows various MC receptor ligands.

TABLE I

Melanocortin Receptor Ligands

| | | |
|---|---|---|
| αMSH: | Ac-SYSMEHFRWGKPV-NH$_2$ | (SEQ ID NO:2) |
| NDP: | Ac-SYS(Nle)EHfRWGKPV-NH$_2$ | (SEQ ID NO:3) |
| γ1-MSH: | YVMGHFRWDRF-OH | (SEQ ID NO:4) |
| γ2-MSH: | H$_2$N-YVMGHFRWDRFG-OH | (SEQ ID NO:5) |
| γ3-MSH: | H$_2$N-YVMGHFRWDRFGRRNGSSSSGVGGAAQ-OH | (SEQ ID NO:6) |
| ACTH$_{(4-10)}$: | MEHFRWG-OH | (SEQ ID NO:7) |
| β∼-MSH: | H$_2$N-AEKKDEGPYRMEHFRWGSPPKE-OH | (SEQ ID NO:8) |
| HP 228: | Ac-(Nle)QHfRwG-NH$_2$ | (SEQ ID NO:9) |

αMSH, α-melanocyte-stimulating hormone; ACTH, adrenocorticotropic hormone; NDP, αMSH analog having Norleucine and D-Phe.

Amino acids provided throughout the application are identified by their well known one letter or three letter codes and as being in the D- or L-configuration by designations "D" or "L," respectively or, alternatively, using lower case letters to designate amino acids in the D-configuration. Where not specified, an amino acid can be in the D- or L-configuration but is more likely in the L-form.

The structural relationship between HP 467 and various MC receptor ligands suggested that HP 467 could function as an MC receptor ligand. As disclosed herein, HP 467 exhibits high affinity binding to MC receptors in rat brain homogenates and in cell lines transfected with various MC receptors (see Examples III and IV).

The invention also provides MC receptor tetrapeptide ligands. A combinatorial library was prepared by the positional scanning format (U.S. Pat. No. 5,556,762, issued Sep. 17, 1996, which is incorporated herein by reference) and screened to find smaller ligands that bind to MC receptors. The present invention thus further provides tetrapeptide ligands that bind to MC receptors. Such tetrapeptides have the structure A1-B2-C3-D4, where "A1" is αFmLys, L-hmP, His, L-Nal, Arg, D-Arg, ε-Lys, Lys, D-pyrala, D-Lys, D-His, D-Ala, Thiopro, L-isoN or 3-2Met; "B2" is Arg, D-Thi, pCl-f, D-Phe, Arg, α-Orn, pF-F, D-His, D-Lys, ε-Lys, δ-Orn, Thiopro, t4-benz, L-hmP or D-Cit; "C3" is Arg, L-Cha, D-Ile, D-Arg, pCl-F, D-Lys, α-Orn, pCl-f, D-Ser, L-hmP, L-pyrala, D-His, Npecot, εAca, D-Cit or Thiopro; and "D4" is D-Nal, D-Arg, D-His, ε-Lys, Lys, D-Lys or D-Glu. Abbreviations of amino acid derivatives used throughout the application are shown in Table II.

As disclosed herein, a positional scanning combinatorial library was constructed to contain 91$^4$ (68,574,960) tetrapeptides having the general structure A1-B2-C3-D4. In positional scanning libraries, a defined amino acid is determined for a given position and is "walked" through the length of the peptide, resulting in the defined amino acid appearing in positions A1, B2, C3 and D4. Mixtures active at each of the four positions can be identified in a single screen. The following peptides were synthesized: Ac-OXXX-NH$_2$; Ac-XOXX-NH$_2$; Ac-XXOX-NH$_2$; and Ac-XXXO-NH$_2$; where "O" is a defined single amino acid and "X" represents a mixture of 91 L-, D- and amino acid derivatives such that each peptide is represented as 91 mixtures each containing 753,571 peptides.

TABLE II

Abbreviations of Amino Acid Derivatives

| Abbreviation | Full Name |
|---|---|
| ε-Aca | ε-aminocaproic acid |
| t4-benz | trans-4-(NHCH$_2$)cyclohexyl-COOH |
| Boc | t-butoxycarbonyl |
| Cbz | benzyloxycarbonyl |
| Cha | cyclohexylalanine |
| Cit | citrulline |
| Fmoc | fluorenylmethoxycarbonyl |
| αFmLys | lysine (α-Fmoc) |
| hmP | homoproline |
| isoN | isoasparagine |
| ε-Lys | αN-Cbz-lysine (Boc) |
| 3-2Met | 3-amino-2-methyl-propionic acid |
| Nal | naphthylalanine |
| Npecot | nipecotic acid |
| α-Orn | ornithine (Cbz) |
| δ-Orn | αN-Cbz-ornithine (Boc) |
| pCl-F | L-4-chlorophenylalanine |
| pCl-f | D-4-chlorophenylalanine |
| pF-F | L-4-fluorophenylalanine |
| pyrala | (3-pyridyl)alanine |
| Thi | (2-thienyl)alanine |
| Thiopro | thioproline |

Using a positional scanning combinatorial library, a number of high affinity tetrapeptide MC receptor ligands were identified (see Example X). Particularly active peptides are provided herein having the structure A1-B2-C3-D4, where "A1" is αFmLys or His; "B2" is Arg, D-Thi, or pCl-f; "C3" is Arg, L-Cha, or D-Ile; and "D4" is D-Nal or D-Arg (see Table V in Example X). Based on results with these peptides, additional peptides were synthesized with the following amino acids in specific positions in the tetrapeptide: αFmLys and His at position "A1"; Arg, D-Thi and pCl-f at position "B2"; Arg, L-Cha and Ile at position "C3"; and D-Nal and D-Arg at position "D4". Synthesis of peptides containing these amino acids resulted in 36 individual tetrapeptides that were tested for activity. Several peptides were found to have high affinity for MC receptors (see Table VI in Example X).

The invention also provides the peptides His-(pCl-f)-Arg-(D-Nal) (SEQ ID NO:10); His-(pCl-f)-(L-Cha)-(D-Arg) (SEQ ID NO:11); (αFmLys)-(pCl-f)-Arg-(Nal) (SEQ ID NO:12); (αFmLys)-Arg-(L-Cha)-(Nal) (SEQ ID NO:13); (αFmLys)-Arg-(L-Cha)-(D-Arg) (SEQ ID NO:14); (αFmLys)-(D-Thi)-Arg-(Nal) (SEQ ID NO:15); (αFmLys)-Arg-Arg-(Nal) (SEQ ID NO:16); and His-(pCl-f)-Arg-(D-Nal) (SEQ ID NO:17). The amino terminus for any of the tetrapeptides disclosed herein can be modified by acetylation and the carboxy terminus can be modified by amidation. As disclosed herein, the peptide Ac-His-(pCl-f)-Arg-(D-Nal)-NH$_2$ (SEQ ID NO:18) is a high affinity MC receptor ligand having an IC$_5$, the inhibitory concentration at which 50% of binding is inhibited, of 18 nM.

MC receptor ligands such as the peptides disclosed herein can be synthesized using a modification of the solid phase peptide synthesis method of Merrifield (*J. Am. Chem. Soc.* 85:2149 (1964), which is incorporated herein by reference) or can be synthesized using standard solution methods well known in the art (see, for example, Bodanszky, M., *Principles of Peptide Synthesis* (Springer-Verlag, 1984), which is incorporated herein by reference). Peptides prepared by the method of Merrifield can be synthesized using an automated peptide synthesizer such as the Applied Biosystems 431A-01 Peptide Synthesizer (Mountain View, Calif.) or using the manual peptide synthesis technique described by Houghten, *Proc. Natl. Acad. Sci., USA* 82:5131 (1985), which is incorporated herein by reference. For example, HP 467 was synthesized as described in Example I.

Peptides can be synthesized using amino acids or amino acid analogs, the active groups of which are protected as required using, for example, a t-butyldicarbonate (t-BOC) group or a fluorenylmethoxy carbonyl (FMOC) group. Amino acids and amino acid analogs can be purchased commercially (Sigma Chemical Co.; Advanced Chemtec) or synthesized using methods known in the art. Peptides synthesized using the solid phase method can be attached to resins including 4-methylbenzhydrylamine (MBHA), 4-(oxymethyl)-phenylacetamido methyl and 4-(hydroxymethyl)phenoxymethyl-copoly(styrene-1% divinylbenzene) (Wang resin), all of which are commercially available, or to p-nitrobenzophenone oxime polymer (oxime resin), which can be synthesized as described by De Grado and Kaiser, *J. Org. Chem.* 47:3258 (1982), which is incorporated herein by reference.

The choice of amino acids or amino acid derivatives incorporated into the peptide will depend, in part, on the specific physical, chemical or biological characteristics required of the MC receptor peptide ligand. Such characteristics are determined, in part, by the route by which the MC receptor ligand will be administered or the location in a subject to which the MC receptor ligand will be directed.

Selective modification of the reactive groups in a peptide also can impart desirable characteristics to an MC receptor ligand. Peptides can be manipulated while still attached to the resin to obtain N-terminal modified compounds such as an acetylated peptide or can be removed from the resin using hydrogen fluoride or an equivalent cleaving reagent, then modified. Compounds synthesized containing the C-terminal carboxy group (Wang resin) can be modified after cleavage from the resin or, in some cases, prior to solution phase synthesis. Methods for modifying the N-terminus or C-terminus of a peptide are well known in the art and include, for example, methods for acetylation of the N-terminus or methods for amidation of the C-terminus. Similarly, methods for modifying side chains of the amino acids or amino acid analogs are well known to those skilled in the art of peptide synthesis. The choice of modifications made to the reactive groups present on the peptide will be determined by the characteristics that are desired in the peptide.

A cyclic peptide also can be an effective MC receptor ligand. A cyclic peptide can be obtained by inducing the formation of a covalent bond between, for example, the amino group at the N-terminus of the peptide and the carboxyl group at the C-terminus. Alternatively, a cyclic peptide can be obtained by forming a covalent bond between a terminal reactive group and a reactive amino acid side chain or between two reactive amino acid side chains. The choice of a particular cyclic peptide is determined by the reactive groups present on the peptide as well as the desired characteristic of the peptide. For example, a cyclic peptide can provide an MC receptor ligand with increased stability in vivo.

A newly synthesized peptide can be purified using a method such as reverse phase high performance liquid chromatography (RP-HPLC) as described in U.S. Pat. No. 5,420,109, issued May 30, 1995, which is incorporated herein by reference. Alternatively, other methods of separation based on the size or charge of the peptide can be used for peptide purification. Furthermore, the purified peptide can be characterized using these and other well known methods such as amino acid analysis and mass spectrometry (see U.S. Pat. No. 5,420,109).

The invention also relates to pharmaceutical compositions comprising an MC receptor ligand such as HP 467 and a pharmaceutically acceptable carrier. Pharmaceutically acceptable carriers are well known in the art and include aqueous solutions such as physiologically buffered saline or other solvents or vehicles such as glycols, glycerol, oils such as olive oil or injectable organic esters.

A pharmaceutically acceptable carrier can contain physiologically acceptable compounds that act, for example, to stabilize the MC receptor ligand or increase the absorption of the agent. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the MC receptor ligand and on the particular physico-chemical characteristics of the specific MC receptor ligand.

The invention further relates to methods of administering a pharmaceutical composition comprising an MC receptor ligand such as HP 467 to a subject in order to restrain pathologically elevated cytokine activity in the subject. For example, HP 467 can be administered to a subject as a treatment for inflammation, pain, cachexia and pathoimmunogenic diseases such as rheumatoid arthritis, inflammatory bowel disease and systemic lupus erythematosus, each of which is characterized by pathologically elevated cytokine activity. As used herein, the term "pathologically elevated" means that a cytokine activity is elevated above a range of activities that is expected in a normal population of such subjects. For example, a normal range of IL-1 activity present in a specific tissue can be determined by sampling a statistically significant number of normal, healthy subjects in the population. A subject having a pathology characterized by cytokine-induced pathological effects can be identified by determining that the cytokine activity in the subject is pathologically elevated above the normal range. In particular, a pathologically elevated level of cytokine activity is at least about one standard deviation above the normal, and can be two standard deviations or greater above the normal range.

A pharmaceutical composition comprising an MC receptor ligand such as HP 467 can be administered to a subject having pathologically elevated cytokine activity by various routes including, for example, orally, intravaginally, rectally, or parenterally, such as intravenously, intramuscularly, subcutaneously, intraorbitally, intracapsularly, intraperitoneally, intracisternally or by passive or facilitated absorption through the skin using, for example, a skin patch or transdermal iontophoresis, respectively. Furthermore, the composition can be administered by injection, intubation or topically, the latter of which can be passive, for example, by direct application of an ointment or powder, or active, for example, using a nasal spray or inhalant. A cytokine restraining agent also can be administered as a topical spray, in which case one component of the composition is an appropriate propellant. The pharmaceutical composition also can be incorporated, if desired, into liposomes, microspheres or other polymer matrices (Gregoriadis, *Liposome Technology*, Vols. I to III, 2nd ed., CRC Press, Boca Raton, Fla. (1993), which is incorporated herein by reference). Liposomes, for example, which consist of phospholipids or other lipids, are nontoxic, physiologically acceptable and metabolizable carriers that are relatively simple to make and administer.

The invention also provides methods of assaying for the presence of an MC receptor in a sample by contacting the sample with a radiolabeled peptide, for example, $^{125}$I-HP 467. The method further consists of removing unbound radiolabeled peptide from the sample and determining the binding of the radiolabeled peptide. In addition to labeling the peptide with a radioactive moiety, the peptide also can be modified to introduce a chemical moiety that can be readily detected, for example, a fluorescent moiety, as long as the introduced chemical moiety does not interfere with binding of the peptide to one or more MC receptors.

The sample is contacted with the radiolabeled peptide under conditions that allow specific binding of the peptide to the sample. One skilled in the art will know or can readily determine conditions that allow specific binding of the radiolabeled peptide to the sample. Such conditions include, for example, temperature, pH and time of incubation. For example, the conditions that allow specific binding of a peptide to a sample are generally about physiological pH, at a temperature between about 4° C. and 37° C., and for a time of about 30 min to 16 hr. Such conditions include, for example, those disclosed in Examples III and IV.

Binding assays of MC receptor transfected cell lines as well as a receptor binding assay in rat brain homogenates have been developed. Initial experiments using a tritiated ligand failed to yield specific binding, so the disclosed assay of the invention was developed using $^{125}$I-HP 467. Mouse L cells and human embryonic kidney (HEK) 293 cell lines were transfected with various MC receptors to determine if HP 467 displayed specificity for MC receptor types. Advantages of HEK 293 cells over L cells for MC receptor assays include the high receptor numbers per cell for all receptors including MC1, tight Scatchard plots for all receptors including MC1, and the human cell origin of the HEK 293 cell lines expressing human receptors, which can reflect MC receptor binding in human better than cell lines from other species.

Binding kinetics and competition with standard analogues confirmed that the binding site of HP 467 is an MC receptor (see Examples III and IV). Thus, the present invention provides a new radioligand for MC receptors, Ac-Nle-Gln-His-(p($^{125}$I)-D-Phe)-Arg-(D-Trp)-Gly-NH$_2$ ($^{125}$I-HP 467).

The effects of HP 467 on cytokines, via its binding to MC receptors, are similar to those for HP 228 (see Examples V through IX). The effect of HP 228 on cytokines and the uses provided thereby are described, for example, in U.S. Pat. No. 5,420,109, WO 95/13086 and WO 96/27386, each of which is incorporated herein by reference. The present invention provides a method of restraining a pathologically elevated cytokine activity in a subject by administering to the subject an effective amount of HP 467. The pathologically elevated cytokine activity can be due, for example, to inflammation, cachexia, or a patho-immunogenic disease. Interestingly, however, HP 467 antagonizes HP 228 induced hypophagia and acute metabolic effects caused by HP 228 (see Examples VIII and IX). Therefore, HP 467 can additionally be used to antagonize HP 228 in the areas of obesity (food intake) and metabolism. In addition, HP 467 can be used as a lead compound for new drug discovery related to antagonism of known MC agonists.

Cytokine expression can result in damage to healthy tissue in a subject and, in extreme cases, can lead to severe disability and death. Cytokines can be expressed at a site of localized infection or can be expressed systemically, for example, in an immune response or in response to bacterial endotoxin-induced sepsis. Cytokine expression can induce pyrexia (fever) and hyperalgesia (extreme sensitivity to pain) in a subject, as well as macrophage and monocyte activation, which produces or further contributes to an inflammatory response in a subject.

Since cytokine expression can be localized or systemic, one skilled in the art would select a particular route and method of administration of HP 467 based on the source and distribution of cytokines in a subject. For example, in a subject suffering from a systemic condition such as bacterial endotoxin-induced sepsis, a pharmaceutical composition comprising HP 467 can be administered intravenously, orally or by another method that distributes the compound systemically. However, in a subject suffering from a pathology caused by localized cytokine expression such as acute respiratory distress syndrome, HP 467 can be suspended or dissolved in the appropriate pharmaceutically acceptable carrier and administered directly into the lungs using a nasal spray or other inhalation device.

In order to restrain the biological activity of a cytokine, HP 467 must be administered in an effective dose, which is about 0.01 to 100 mg/kg body weight. The total effective dose can be administered to a subject as a single dose, either as a bolus or by infusion over a relatively short period of time, or can be administered using a fractionated treatment protocol, in which the multiple doses are administered over a more prolonged period of time. One skilled in the art would know that the concentration of HP 467 required to obtain an effective dose in a subject depends on many factors including the age and general health of the subject as well as the route of administration and the number of treatments to be administered. In view of these factors, the skilled artisan would adjust the particular dose so as to obtain an effective dose for restraining cytokine activity.

Examples of the effectiveness of HP 467 in preventing or minimizing adverse biological effects mediated by cytokines are provided in Examples V through IX and summarized in Table IV. HP 467 can effectively restrain cytokine expression in mice and provide relief from cytokine-mediated swelling and lethality. Thus, HP 467 can be used as a medicament for the treatment of pathologies such as inflammation, pain, cachexia and patho-immunogenic diseases such as arthritis, inflammatory bowel disease and systemic lupus erythematosus, which are characterized by altered cytokine activity.

The following examples are intended to illustrate but not limit the invention.

EXAMPLE I

Synthesis of HP 467

This example provides a standard preparation of HP 467.

HP 467 was synthesized essentially as described in U.S. Pat. No. 5,420,109. Briefly, 100 mg MBHA resin containing a t-Boc Gly derivative was added to a reaction vessel suitable for solid phase peptide synthesis (Houghten, *Proc. Natl. Acad. Sci. USA* 82:5131 (1985), which is incorporated herein by reference). The following conditions were used for peptide synthesis: coupling was performed in 6-fold excess in N,N-dimethylformamide (DMF) with 0.2 M N-hydroxybenzotriazole(HOBt) and 0.2 M N,N-diisopropylcarbodiimide (DIC) for 90 minutes; activation was performed with 5% diisopropylethylamine (DIEA) in methylene chloride (DCM) for three washes of 2 min; deprotection was performed with 55% trifluoroacetic acid (TFA) for 30 min; washes were performed with DCM and isopropyl alcohol (IPA); the ninhydrin test was run after washing with DMF, DCM and methanol; acetylation was performed with acetylimidazole in 40-fold excess DCM for 4 hr; and cleavage was performed with hydrofluoric acid (HF) and anisole for 90 min.

Peptide synthesis was carried out with the sequential steps of activation, coupling of amino acid, ninhydrin test, deprotection and washing, and the steps were repeated for addition of a new amino acid at each cycle. The amino acids were coupled in the order D-Trp, L-Arg, p-iodo-D-Phe, L-His, L-Gln and L-Nle. The peptide was acetylated and the DNP protecting group was removed from His using 2.5% thiophenol in DMF followed by removal of formyl protecting groups in 25% HF in dimethyl-sulphide. The peptide was cleaved from the resin and processed as described previously (U.S. Pat. No. 5,420,109). The resulting peptide was approximately 80 to 90% pure.

EXAMPLE II

Peptide Iodination

This example provides methods for iodinating a peptide.

For diazotization, 1.0 ml 2 N $H_2SO_4$ was added to 3.0 mg peptide containing p-$NH_2$-Phe. A 6.67 µl aliquot (0.02 µmol) was transferred to a reaction vial, and 79.3 µl of 2 N $H_2SO_4$ was added. A 6.90 µl aliquot (0.02 µmol) of 3 mM $NaNO_2$ was added, and the reaction was incubated at 0° C. for 30-40 min.

For iodination, 100 µl 2 N $H_2SO_4$ and 400 µl 0.5 M $CuSO_4$ was added to 12.0 mg Zn powder, and the components were allowed to react with periodic mixing for 30–45 min, with venting, until bubbling stopped. The grains were washed twice with $H_2O$. For unlabeled peptide, 7.12 µl of 0.67 mM NaI (0.0047 µmol) was added to the reaction vial. For radiolabeled peptide, 0.0047 µmol of Na $^{125}$I was added to the reaction vial. Approximately ⅛ of the copper grains was added to the vial, and the vial was vortexed 1 min. The reaction was carried out vented at room temperature for 3 hr with periodic mixing.

Samples were analyzed on a Vydac 218TP54 C-18 column and were monitored at 214 nm. Buffer A was 0.05% TFA in $H_2O$, and Buffer B was 0.05% TFA in acetonitrile. Samples were resolved using a 2% per minute gradient from 5 to 55% Buffer B in 25 min.

Using the method described in this example, $^{125}$I-HP 467 was routinely labeled to a specific activity of 2000 Ci/mmol. These results demonstrate that HP 467 can be iodinated to generate unlabeled iodo-peptide or high specific activity radiolabeled iodo-peptide.

EXAMPLE III

Melanocortin Receptor Binding Assay Using $^{125}$I-HP 467 In Rat Brain Homogenate This example provides a binding assay using $^{125}$I-HP 467 to detect MC receptors in rat brain homogenate.

For assays, fine chemicals were obtained from Sigma (St. Louis Mo.) and GF/B plates and MICROSCINT were obtained from Packard Instrument Co. (Meriden Conn.). Frozen rat brains were thawed and the thalamus and hypothalamus were dissected out and weighed. The tissue was homogenized in 40 ml buffer A (50 mM Tris-HCl, 2 mM EDTA, 10 mM $CaCl_2$, 100 µM PMSF, pH 7.4) in a Dounce homogenizer. The homogenate was centrifuged at 39,000×g for 10 min, resuspended in 20 ml fresh buffer and recentrifuged. The pellet was resuspended in 80 ml buffer B (50 mM Tris-HCl, 2 mM EDTA, 10 mM $CaCl_2$, 5 mM $MgCl_2$, 100 µM PMSF, pH 7.4). $^{125}$I-HP 467 was custom labeled by Amersham to a specific activity of 2000 Ci/mmol (Amersham; Arlington Heights IL). Fifty pM $^{125}$I-HP 467 and 0.2 mg protein/ml membrane suspension containing 2 mg/ml BSA was added to each assay tube.

Typical assay volumes were 50 µl $^{12}$I-HP 467, 50 µl HP 228 and 250 µl membrane. Competition assays were performed using α-MSH, γ1-MSH, γ2-MSH, γ3-MSH and ACTH (4–10) also containing 1 mM phenanthroline, 200 µg/ml bacitracin, and 5 µg/ml leupeptin. Tubes were incubated for 2 hours at 37° C. The assay was terminated by filtration through GF/B filters previously soaked in 5 mg/ml BSA Tris-HCl buffer. The samples were washed with Tris-HCl, dried and counted in Packard Minaxl gamma counter (Packard Instrument Co.).

Binding was found to be tissue specific with most binding observed in rat hypothalamus. As shown in FIGS. 1 to 4, binding of $^{125}$I-HP 467 was saturable. Saturation binding curves of $^{125}$I-HP 467 bound to rat brain membranes indicated a Kd of 0.4 nM and a Bmax of 21 fmoles/mg protein.

These results demonstrate that $^{125}$I-HP 467 can be used in a binding assay to detect MC receptors in rat brain homogenates.

EXAMPLE IV

Melanocortin Receptor Binding Assay Using $^{125}$I-HP 467 in Transfected Cells

This example demonstrates the use of $^{125}$I-HP 467 for assaying MC receptor binding in human and mouse cell lines transfected to express MC receptors.

All cell culture media and reagents were obtained from GibcoBRL (Gaithersburg Md.), except for COSMIC CALF SERUM (HyClone; Logan Utal.). HEK 293 and mouse L cell lines were transfected with the human MC receptors hMC1, hMC3, and hMC4 (Gantz et al., *Biochem. Biophys. Res. Comm.* 200:1214–1220 (1994); Gantz et al., *J. Biol. Chem.* 268:8246–8250 (1993); Gantz et al. *J. Biol. Chem.* 268:15174–15179 (1993); Haskell-Leuvano et al., *Biochem. Biophys. Res. Comm.* 204:1137–1142 (1994); each of which is incorporated herein by reference). Vectors for construction of an hMC5 expressing cell line were obtained, and a line of HEK 293 cells expressing hMC5 was constructed (Gantz, supra, 1994). hMC5 has been described previously (Franberg et al., *Biochem. Biophys. Res. Commun.* 236:489–492 (1997); Chowdhary et al., *Cytogenet. Cell Genet.* 68:1–2 (1995); Chowdhary et al., *Cytogenet. Cell Genet.* 68:79–81 (1995), each of which is incorporated herein by reference). L cell lines were maintained in MEM containing 25 nM HEPES, sodium pyruvate, 10% COSMIC CALF SERUM, 100 units/ml penicillin, 100 µg/ml streptomycin, and 0.2 mg/ml G418 to maintain selection. For HEK 293 cells, DMEM was used instead of MEM, and 2 mM glutamine, non-essential amino acids, and vitamins were included in addition to the above mentioned additives.

Before assaying, cells were washed once with phosphate buffered saline ("PBS"; without $Ca^{2+}$ and $Mg^{2+}$), and stripped from the flasks using 0.25% trypsin and 0.5 mM EDTA. Cells were suspended in PBS, 10% COSMIC CALF SERUM and 1 mM $CaCl_2$. Cell suspensions were prepared at a density of $2 \times 10^4$ cells/ml for HEK 293 cells expressing hMC3, hMC4 or hMC5, and $1 \times 10^5$ cells/ml for HEK 293 cells expressing hMC1. For L cells, cells expressing MC3 or MC4 were suspended at $2 \times 10^5$ cells/ml, and cells expressing MC1 suspended at $8 \times 10^5$ cells/ml. Suspensions were placed in a water bath and allowed to warm to 37° C. for 1 hour.

Binding assays were performed in a total volume of 250 µl for HEK 293 cells, and a volume of 600 µl for L cells. Peptides and other compounds were dissolved in distilled water. $^{125}$I-HP 467 (2000 Ci/mmol) was prepared in 50 mM Tris, pH 7.4, 2 mg/ml BSA, 10 mM $CaCl_2$, 5 mM $MgCl_2$, 2 mM EDTA and added to each tube, with 50,000 dpm for HEK 293 assays or 100,000 dpm for L cell assays. To each tube was added $4 \times 10^3$ HEK 293 cells expressing hMC3, hMC4 or hMC5, or $2 \times 10^4$ cells expressing hMC1. For L cells expressing hMC3 or hMC4, $1 \times 10^5$ cells were used, and for L cells expressing hMC1, $4 \times 10^5$ cells were used. Assays were incubated for 2.5 hr at 37° C.

GF/B filter plates were prepared by soaking for at least one hour in 5 mg/ml BSA and 10 mM $CaCl_2$. Assays were filtered using a Brandel 96-well cell harvester (Brandel Inc.; Gaithersburg, Md.). The filters were washed four times with cold 50 mM Tris, pH 7.4, the filter plates were dehydrated for 2 hr and 35 µl of MICROSCINT was added to each well. Filter plates were counted using a Packard Topcount (Packard Instrument Co.) and data analyzed using GraphPad PRISM v2.0 (GraphPad Software Inc.; San Deigo Calif.) and Microsoft EXCEL v5.0a (Microsoft Corp.; Redmond Wash.).

Binding assays were performed in duplicate in a 96 well format utilizing a 1.2 ml cluster tube system (Corning Costar; Cambridge Mass.). HP 467 was prepared in 50 mM Tris, pH 7.4, and $^{125}$I-HP 467 was diluted to give 100,000 dpm per 50 µl. Serial dilutions (10-fold or 5-fold) of HP 228, α-MSH, NDP and unlabeled HP 467 were prepared from 1.2 mM stock solutions. All assay tubes contained 50 µl of $^{125}$1I-HP 467 and 50 µl of either Tris buffer (for determination of total binding) or diluted peptide (serial dilutions of HP 228, α-MSH, NDP or unlabeled HP 467).

Saturation binding experiments were performed in duplicate in the same volume with the same number of cells as described above for the binding assay. Saturation radioligand binding experiments measure specific radioligand binding at equilibrium at various concentrations of the radioligand. Scatchard analysis of the data was used to determine receptor number and ligand affinity. $^{125}$I-HP 467 was added to the assay, with $2 \times 10^8$ dpm being the highest concentration and 2-fold serial dilutions made thereafter to obtain 8 to 12 data points. Nonspecific binding was determined in the presence of unlabeled HP 467 at 1000 times the concentration of the $^{125}$I-HP 467. The actual amount of tracer added was determined by gamma counting the test tubes on a Packard Minaxl gamma counter. The concentration of $^{125}$I-HP 467 in the assay was calculated from the half-life corrected dpm using EXCEL v5.0a.

Figure 5:
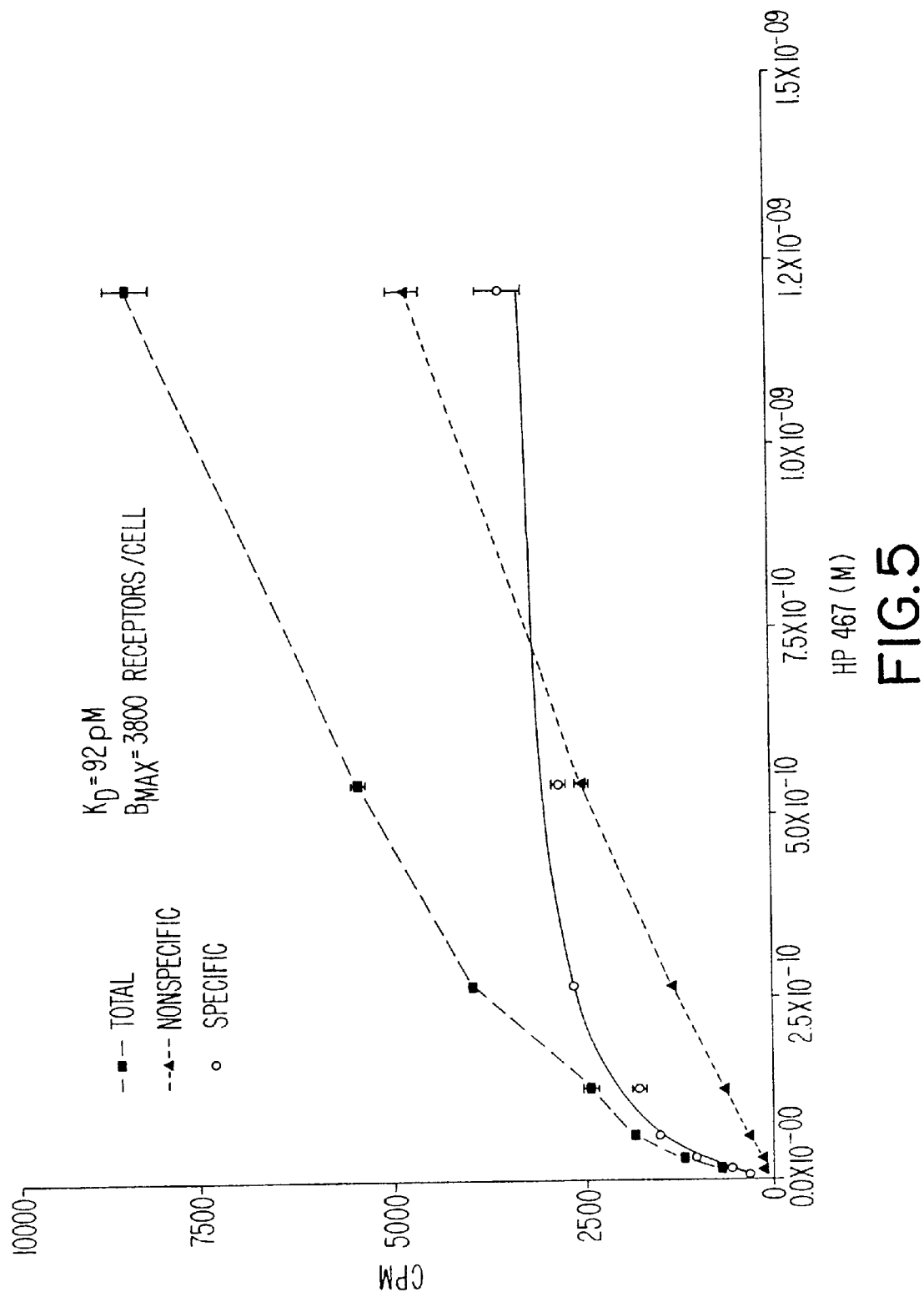
FIG. 5 shows an HP 467 saturation binding curve of mouse L cells expressing melanocortin receptor 1 (MC1).
Figure 6:
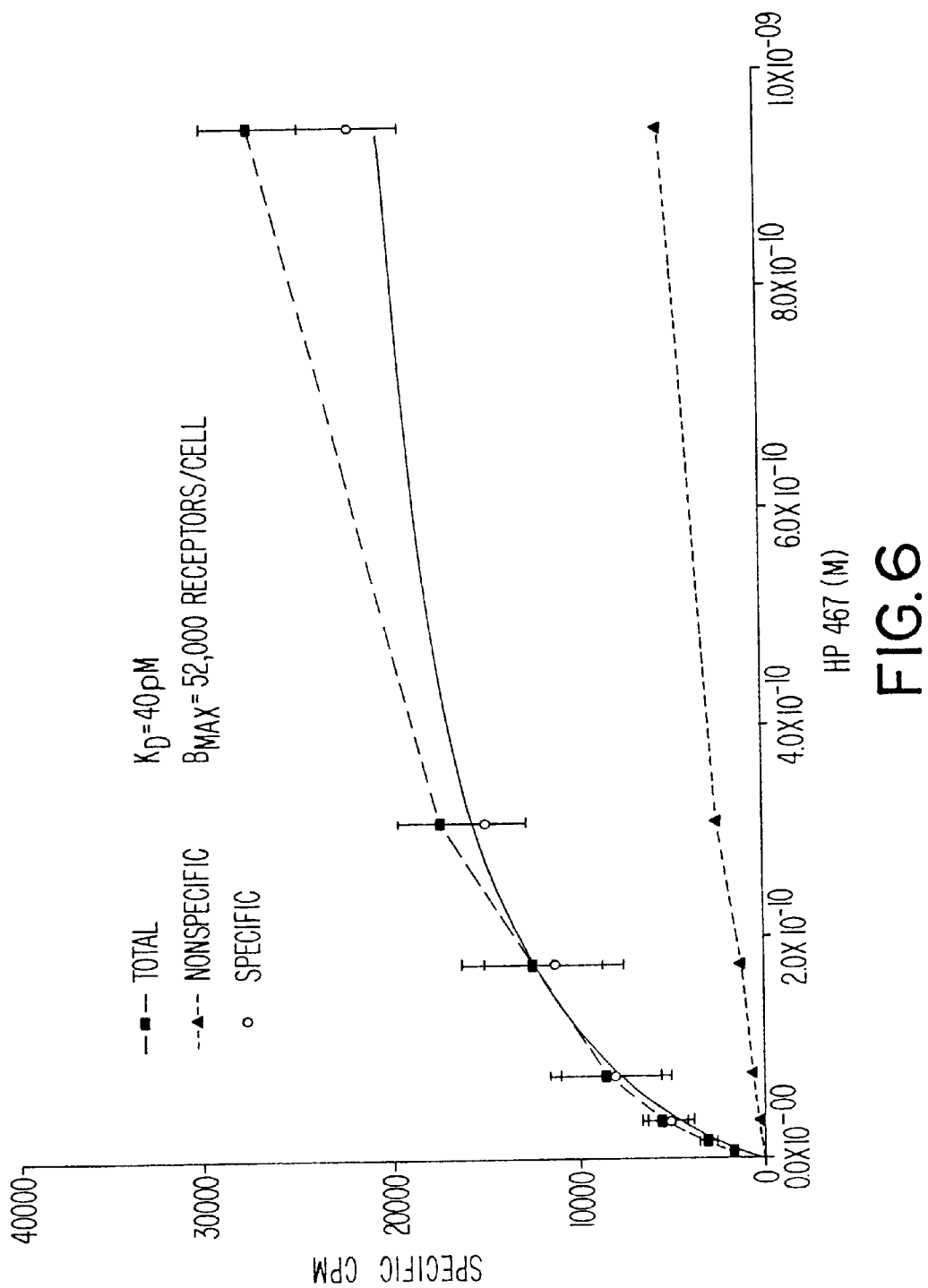
FIG. 6 shows an HP 467 saturation binding curve of mouse L cells expressing melanocortin receptor 3 (MC3).
Figure 8A:
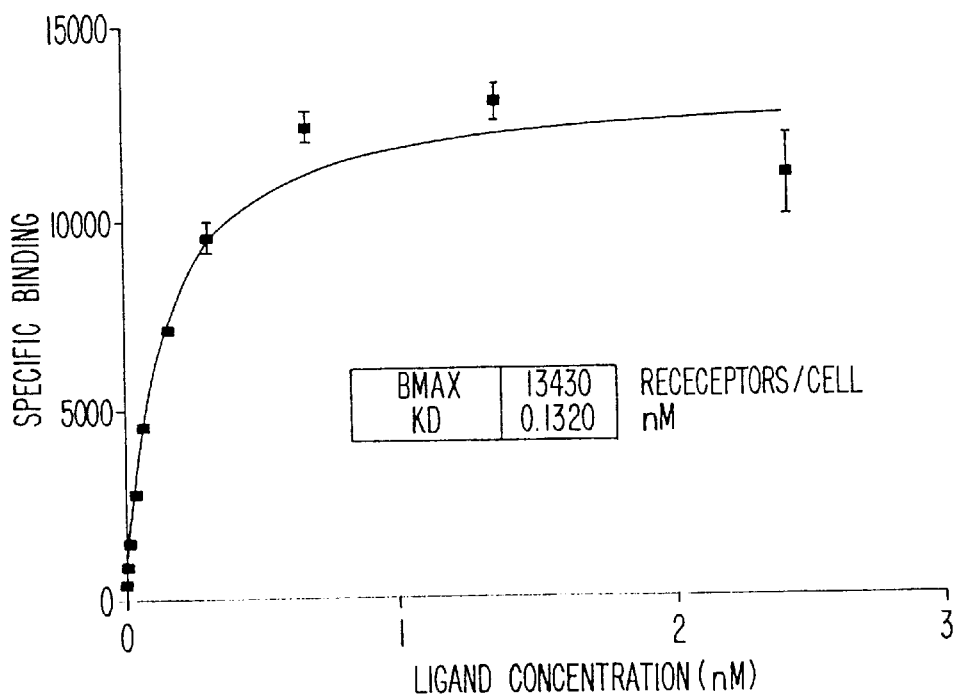
FIG. 8 shows a saturation binding isotherm for HP 467 on human embryonic kidney (HEK) 293 cells expressing MC1.
Figure 8B:
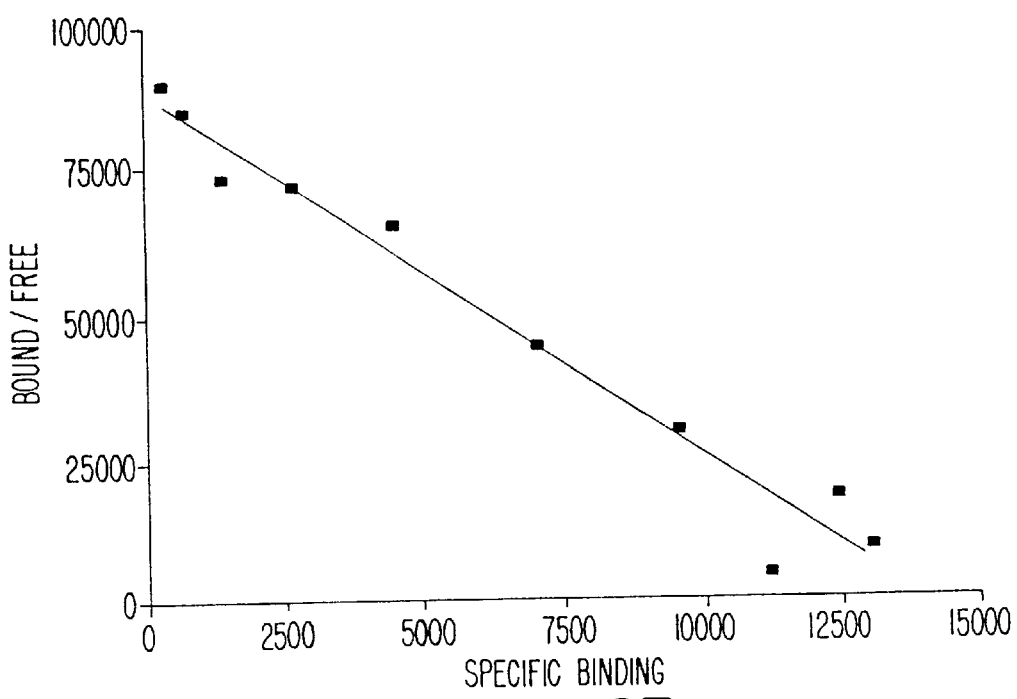
Figure 9A:
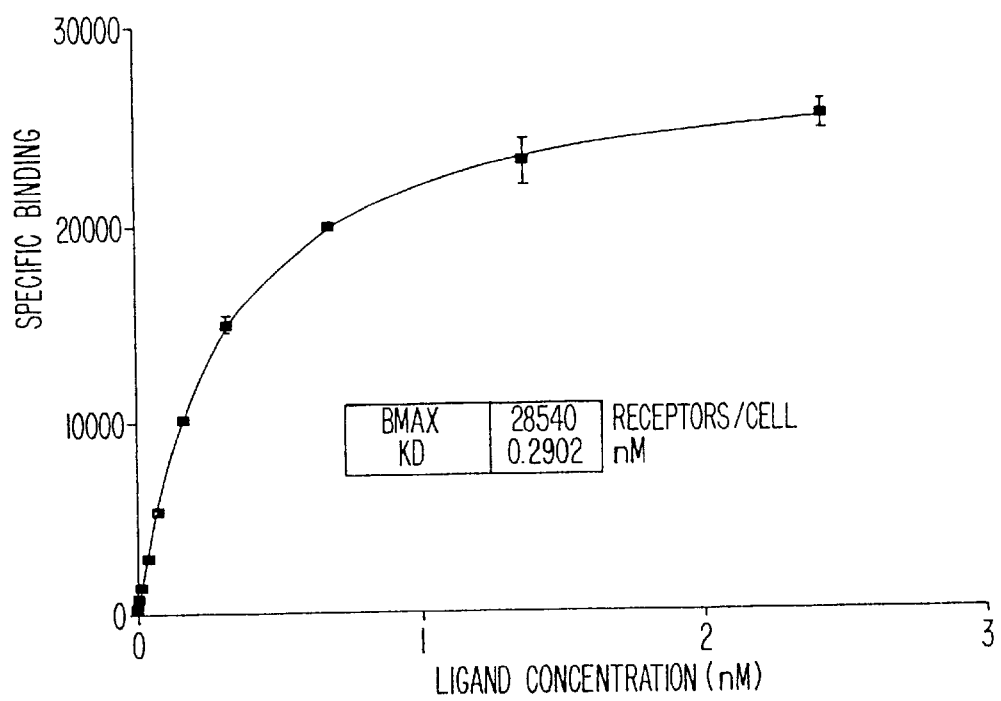
FIG. 9 shows a saturation binding isotherm for HP 467 on HEK 293 cells expressing MC3.
Figure 9B:
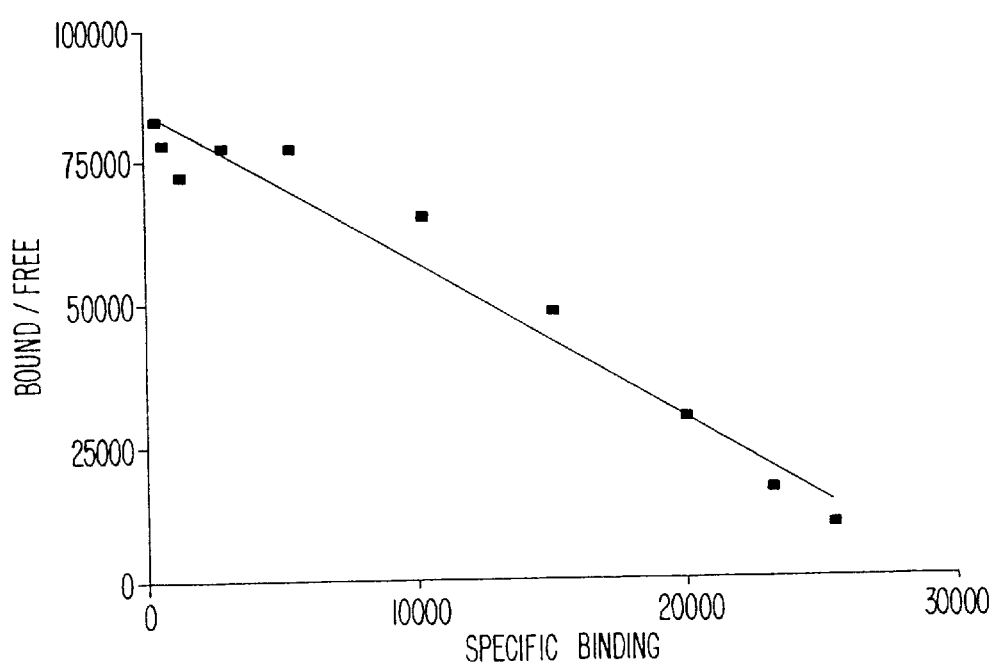
Figure 10A:
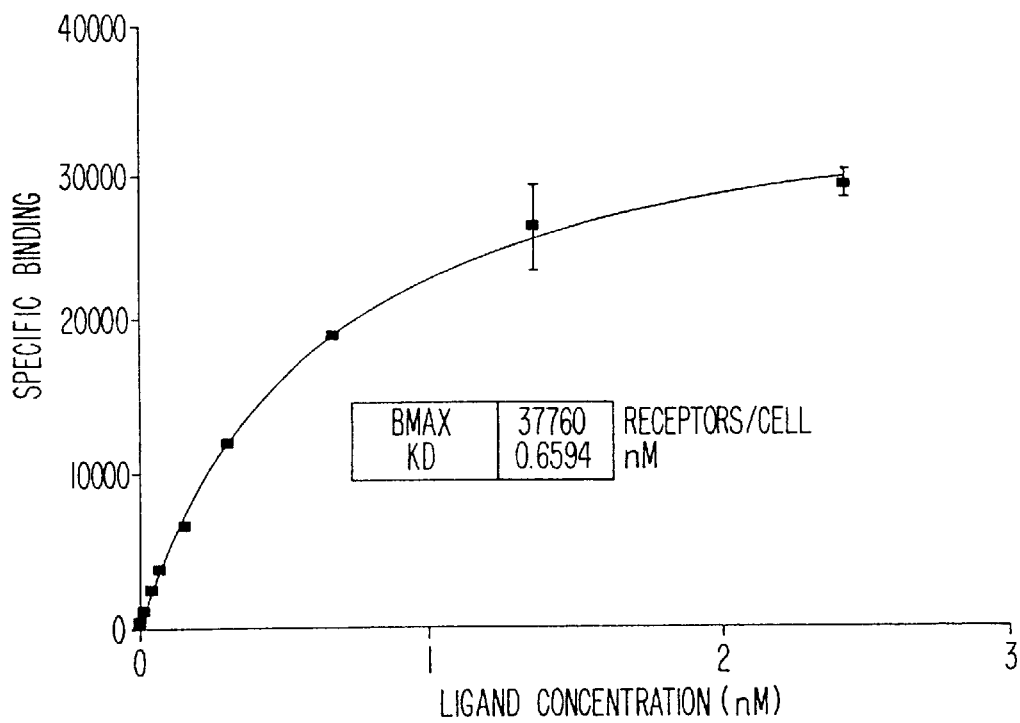
FIG. 10 shows a saturation binding isotherm for HP 467 on HEK 293 cells expressing MC4.
Figure 10B:
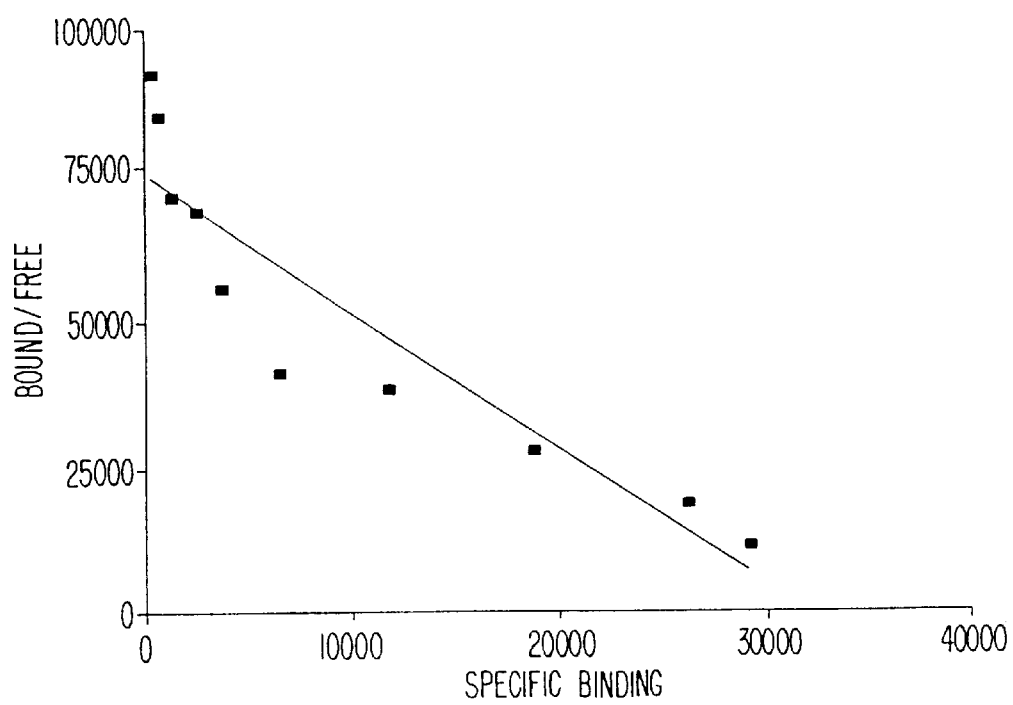
Figure 11A:
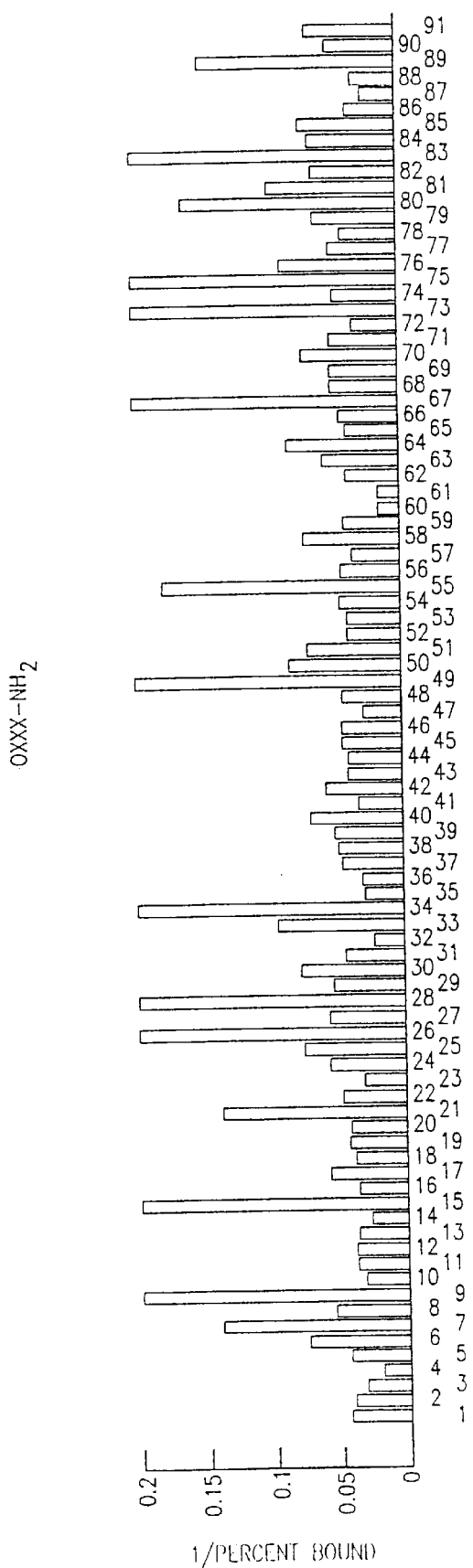
FIG. 11 shows the percent bound for all library mixtures of a tetrapeptide scanning combinatorial library.
Figure 11B:
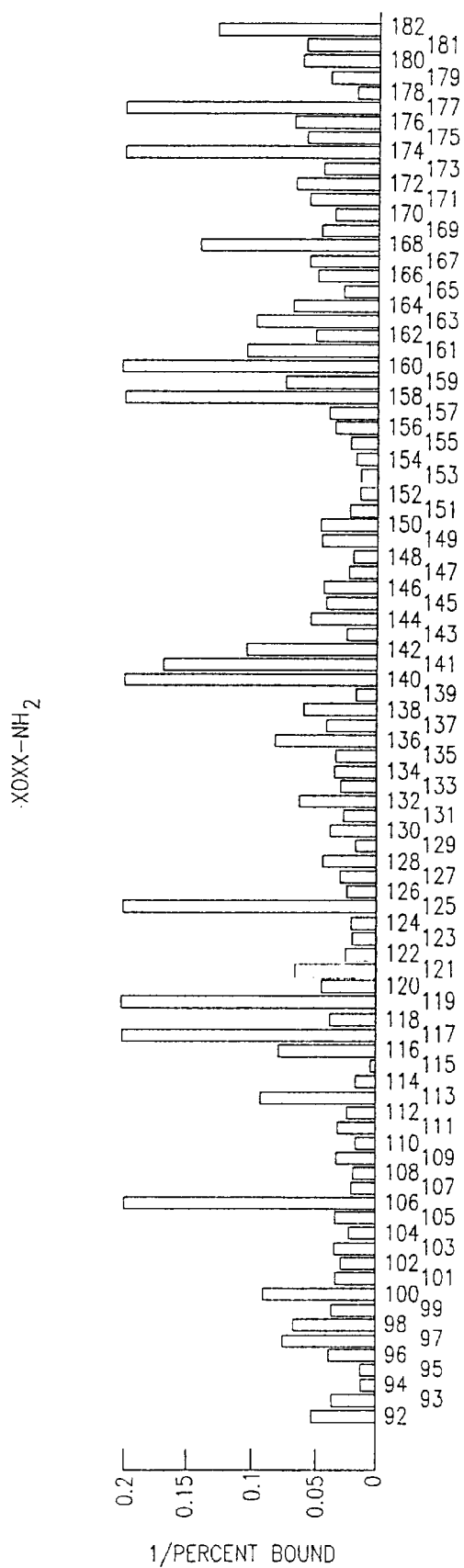
Figure 11C:
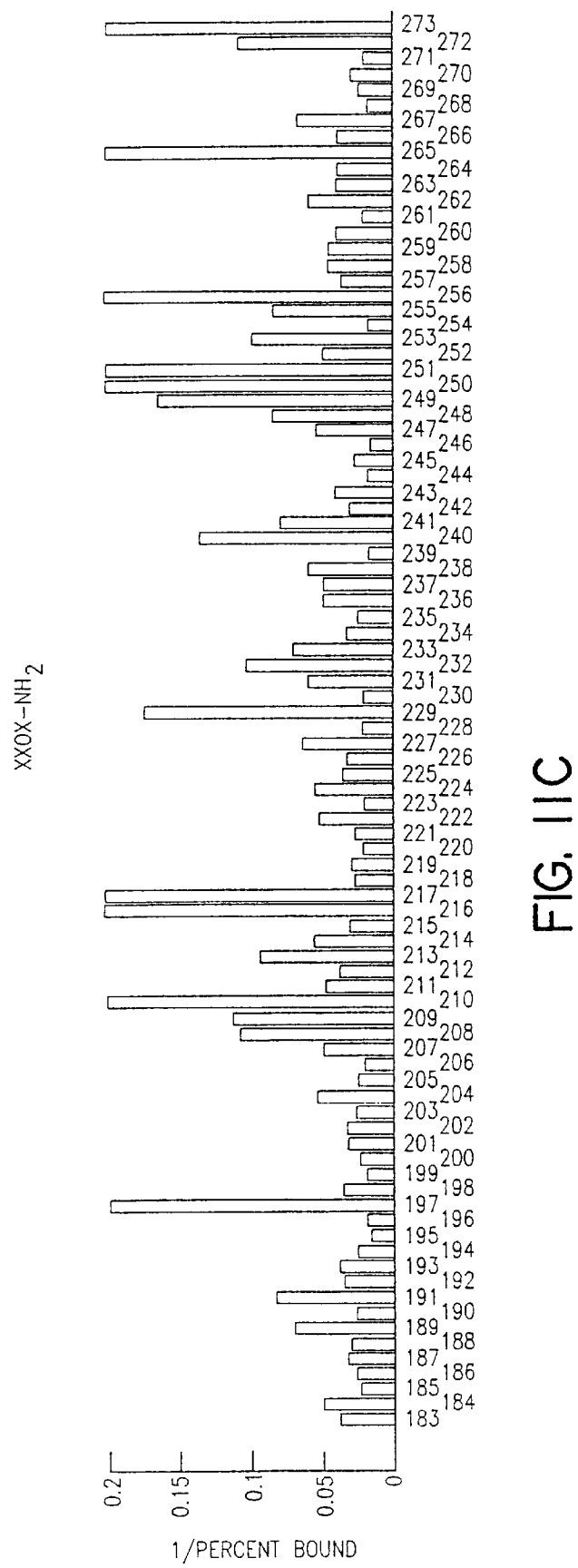
Figure 11D:
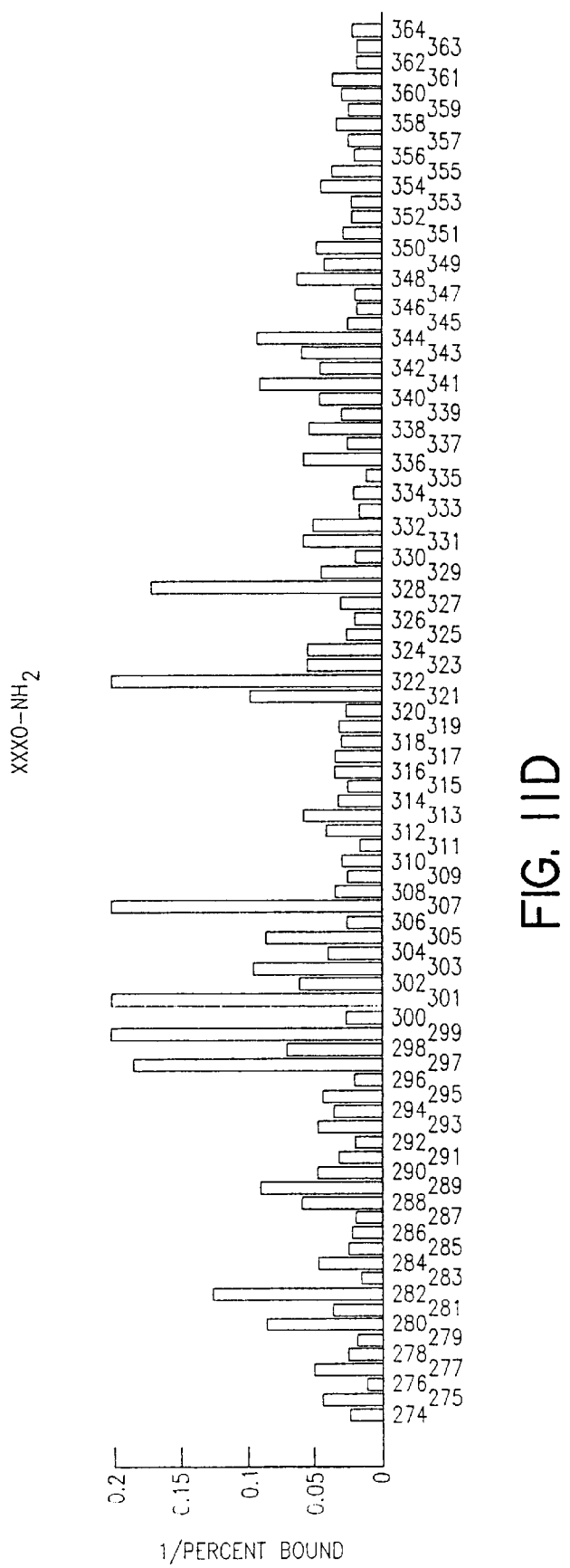

The results of displacement binding assays using L cells for MC receptors hMC1, hMC3, and hMC4 are summarized in Table III. Saturation curves for the L cells are shown as FIGS. 5, 6 and 7 for MC1, MC3 and MC4, respectively. The $K_i$ apparent and displacement binding assays determined from receptor binding assays for hMC5 in HEK 293 cells also are included in Table III. Saturation binding isotherms and Scatchard plots for MC1, MC3 and MC4 in HEK 293 cells are included as FIGS. 8, 9 and 10, respectively. BMAX is indicated as receptors/cell and KD is nM.

As shown in FIGS. 5 through 10, $^{125}$I-HP 467 can bind to the MC receptors MC1, MC3 and MC4. As shown in Table III, $^{125}$I-HP 467 also binds to the MC5 receptor. The binding of $^{125}$I-HP 467 can be displaced by various MC receptor ligands with differing $IC_{50}$ values depending on the specific MC receptor expressed in the cell line.

TABLE III

DISPLACEMENT OF $^{125}$I-HP 467

| PEPTIDE | | RECEPTOR | | | |
|---|---|---|---|---|---|
| | | MC-1 | MC-3 | MC-4 | MC-5 |
| HP 228 | Binding $IC_{50}$ | 1.49 | 29.70 | 7.51 | 194.50 |
| | S. Dev. | 0.78 | 5.23 | 2.95 | 78.49 |
| | n | 3 | 4 | 4 | 2 |
| HP 467 | Binding $IC_{50}$ | 0.23 | 0.48 | 0.31 | 0.46 |
| | S. Dev. | 0.17 | 0.25 | 0.20 | 0.25 |
| | n | 11 | 15 | 14 | 6 |
| α-MSH | Binding $IC_{50}$ | 9.31 | 21.52 | 98.12 | |
| | S. Dev. | 6.41 | 7.92 | 30.24 | |
| | n | 4 | 6 | 5 | 0 |
| NDP | Binding $IC_{50}$ | 1.90 | 2.01 | 4.36 | 5.85 |
| | S. Dev. | 1.44 | 1.53 | 2.79 | 1.92 |
| | n | 5 | 5 | 6 | 2 |

"S. Dev." is the Standard Deviation; "n" represents the number of samples. HP 467, Ac-Nle-Gln-His-(p(I)-D-Phe)-Arg-(D-Trp)-Gly-NH$_2$ (SEQ ID NO:1); HP 228, α-MSH and NDP are as shown in Table I. MC1, MC3 and MC4 receptors were expressed in mouse 10 L cells and MC5 in HEK 293 cells. Concentrations ranged from $10^{-5}$ to $10^{-14}$ M.

EXAMPLE V

Reduction of Lipopolysaccharide-Induced Tumor Necrosis Factor Levels in Mice

This example describes the effectiveness of HP 467 for decreasing tumor necrosis factor (TNF) levels in lipopolysaccharide (LPS; endotoxin) treated mice.

BALB/c female mice weighing approximately 20 g were placed into a control group and three HP 467 treatment groups. Five mg/kg of LPS in 0.9% saline was administered by intraperitoneal (IP) injection to all mice. Mice in the treatment group received either 30, 150 or 300 µg of HP 467 per mouse in a volume of 100 µl. Control mice received 100 µl of saline alone. One minute after initial injections all mice received the LPS injection.

Blood samples were collected from the orbital sinus of treated and control mice 90 minutes after LPS administration. The plasma was separated by centrifugation at 3000×g for 5 min and stored at −20° C. Samples were thawed and diluted with four volumes of 1×PBS (pH 7.4) containing 1% bovine serum albumin. A 100 µl sample of plasma was assayed by ELISA for TNF-α (Genzyme; Cambridge Mass.).

The mean (+SEM) TNF-α level in five mice from each group was determined and the percent reduction in TNF-α levels was calculated. As shown in Table IV, treatment of mice with HP 467 decreased the levels of TNF-α in a dose dependent manner when compared to saline controls with a 3% decrease observed with 30 µg/mouse, a 78% decrease with 150 µg/mouse and an 81% decrease with 300 µg/mouse.

These results indicate that HP 467 can restrain LPS-induced cytokine activity.

TABLE IV

BIOLOGICAL DATA FOR HP 467

| Biological Test | Dose | Efficacy |
|---|---|---|
| Reduction in TNF levels | 30 μg/mouse | 3% |
|  | 150 μg/mouse | 78% |
|  | 300 μg/mouse | 81% |
| Inhibition of LPS-Induced lethality | 300 μg/mouse BID | 50% |
|  | 500 μg/mouse TID | 40% |
| Reduction in arachidonic acid-induced ear swelling | 100 μg/mouse | 82% |

Antagonism of HP 228

| | | Change | |
|---|---|---|---|
| | Drug/Dose | Day 1 | Day 2 |
| Hypophagia (food intake) | Saline | +5.3% | +12.1% |
|  | HP 228 (1.5 mg/Kg) | −6.8% | −5.3% |
|  | HP 228/HP 467 | +2.1% | +4.8% |
| Oxygen Consumption | HP 228/HP 467 (5 mg/kg/10 mg/kg) | 50% of HP 228 | |

HP 228, Ac-(Nle) QHfRwG-NH$_2$ (SEQ ID NO:9); HP 467, Ac-Nle-Gln-His-(p(I)-D-Phe)-Arg-(D-Trp)-Cly-NH$_2$ (SEQ ID NO:1))

EXAMPLE VI

Lipopolysaccharide-Induced Lethality

This example describes the effectiveness HP 467 in reducing lethality from sepsis induced by administration of LPS.

These experiments were performed based on information reported by Rivier et al., *Endocrinology* 125:2800–2805 (1989), which is incorporated herein by reference. Adult female BALB/c mice were provided food and water ad libitum. Mice were treated either IP every 8 hours (three times a day; TID) for 40 hours with 500 μg HP 467 in 200 μl saline or at 8 AM and 4 PM (twice a day; BID) for 40 hours with 300 μg of HP 467 in 200 μl saline. Control animals received injections of saline at the respective times of HP 467 treatment. Immediately following the first injection, 0.6 mg LPS endotoxin in 200 μl saline was administered to each mouse. All groups contained 10 mice.

As shown in Table IV, administration of HP 467 in both dosing regimens significantly increased survival as compared to the saline control mice. There was a 50% survival rate with the BID treatment regimen using HP 467 (300 μg/mouse) and a 40% survival rate with the TID treatment regiment using HP 467 (500 μg/mouse). All mice in the saline control group died within the 40 hours of the study (100% mortality).

These results show that HP 467 significantly inhibits LPS-induced lethality.

EXAMPLE VII

Reduction of Arachidonic Acid-Induced Ear Swelling in Mice

This example demonstrates that HP 467 can reduce arachidonic acid-induced ear swelling in mice.

Experiments were performed using female BALB/c mice weighing 18 to 23 grams. Saline or 100 μg HP 467 was administered IP, 30 minutes prior to topical application of arachidonic acid (Calbiochem-Novabiochem; San Diego Calif.). A 10 μl pipette was used to apply 10 μl of a 100 mg/ml arachidonic acid solution in acetone to the inner and outer surfaces of the right ear of each mouse. Ten ml of acetone (alone) was applied to the inner and outer surface of the left ear of each mouse.

Ear thickness was measured with a hand held spring loaded caliper 60 minutes after arachidonic acid application. Increase in ear thickness was calculated by subtracting the thickness of the control ear from the thickness of the arachidonic acid-treated ear. The value for each group is the average of the swelling observed in the mice of each group. The percent reduction in swelling is based on the swelling observed in the saline control group. As shown in Table IV, HP 467 reduced the level of arachidonic acid-induced ear swelling by 81%.

These results show that HP 467 significantly reduces arachidonic acid-induced ear swelling.

EXAMPLE VIII

HP 467 Antagonism of HP 228 Induced Hypophagia

HP 228 reduces body weight (see WO 96/27386). This example shows that HP 467 antagonizes the effect of HP 228-induced hypophagia, thereby reversing the undesirable decrease in food consumption that occurs following HP 228 administration.

Male Sprague-Dawley rats weighing 250 to 300 grams were divided into three treatment groups of 8 rats each. The control group received IP saline injections BID (1 ml/kg) at 8 AM and 4 PM. Two groups of rats received HP 228 injections IP (1.5 mg/kg) at the same dosing schedule as the control group. After each injection, each rat immediately received a second injection. The second injection for the saline group and one HP 228 group was another injection of saline (1 ml/kg), and the second injection for the remaining HP 228 group was HP 467 at a dose of 3.0 mg/kg. All injections started at 4 PM on day 0 and ended on the afternoon of day 2. Food consumption and body weight measurements were taken daily, each morning.

As shown in Table IV, food intake in the saline control group increased daily as expected. HP 228 treatment caused a decrease in food consumption during the study period, and HP 467 reduced the decrease in food consumption caused by administration of HP 228. These results demonstrate that HP 467 antagonizes the effect of HP 228-induced hypophagia.

EXAMPLE IX

HP 467 Antagonism of Acute Metabolic Effects by HP 228

Weight loss observed with HP 228 correlates to an increased metabolic rate as determined by increased resting oxygen consumption (see WO 96/27386). This example shows that HP 467 antagonizes the acute metabolic effects caused by HP 228 administration.

Male Sprague-Dawley rats (250 to 350 grams) were divided into three treatment groups for the measurement of acute metabolic effects. All injections were administered IP. PBS (1 ml/kg) was administered to two of the groups. The third group received 10 mg/kg HP 467. Fifteen minutes after the initial injections, one PBS group received another injection of PBS (1 ml/kg) and the second group received 5 mg/kg HP 228. The group receiving the initial injection of HP 467 received 5 mg/kg HP 228. Immediately after the second injection the rats were placed into the Oxymax System (Columbus Instruments; Columbus OH) for monitoring. Data was collected 10 minutes after the animal was acclimated to the cage and continued for a total of 50 minutes. The parameters measured were resting oxygen consumption ($VO_2$), resting respiratory quotient (RQ), and total locomotor activity. As shown in Table IV, HP 467 attenuated the effects of HP 228 on $VO_2$.

These results demonstrate that HP 467 antagonizes the effect of HP 228 on food intake and oxygen consumption.

EXAMPLE X

Tetrapeptide Ligands for Melanocortin Receptors

This example demonstrates the use of a positional scanning combinatorial library to identify tetrapeptide ligands for MC receptors.

A positional scanning combinatorial library was constructed to contain $91^4$ (68,574,960) tetrapeptides of the structure A1-B2-C3-D4. In positional scanning libraries, a defined amino acid is determined for a given position and is "walked" through the length of the peptide, resulting in the defined amino acid appearing in positions A1, B2, C3 and D4. Mixtures active at each of the four positions can be identified in a single screen. The following peptides were synthesized: Ac-OXXX-$NH_2$; 91 mixtures each containing 753,571 peptides; Ac-XOXX-$NH_2$; 91 mixtures each containing 753,571 peptides; Ac-XXOX-$NH_2$; 91 mixtures each containing 753,571 peptides; Ac-XXXO-$NH_2$; 91 mixtures each containing 753,571 peptides; where "O" is a defined single amino acid and "X" represents a mixture of 91 L-, D- and amino acids derivatives.

FIG. 11 shows the percent bound for all library mixtures prepared from the positional scanning combinatorial library. Table V shows the $IC_{50}$ for the most active mixtures from the screening data. $IC_{50}$ values were determined in brain tissue as described in Example III.

Based on the results shown in Table V, peptides were synthesized with the following amino acids in specific positions in the tetrapeptide: αFmLys and His at position A1; Arg, D-Thi and pCl-f at position B2; Arg, L-Cha and Ile at position C3; and D-Nal and D-Arg at position D4. Synthesis of peptides containing these amino acids resulted in 2×3×3×2=36 individual tetrapeptides.

TABLE Va $IC_{50}$ values for most active mixtures from the screening data

| Library No. | OXXX | $IC_{50}$ μM | Library No. | XOXX | $IC_{50}$ μM |
|---|---|---|---|---|---|
| 73 | αFinLys | 88 | 106 | R | 14 |
| 83 | L-hmp | 118 | 168 | D-Thi | 224 |
| 7 | H | 122 | 160 | pCl-f | 235 |
| 55 | L-Nal | 155 | 116 | f | 238 |
| 15 | R | 158 | 125 | r | 281 |
| 34 | r | 203 | 141 | α-Orn | 283 |
| 49 | ε-Lys | 214 | 161 | pF-F | 335 |
| 9 | K | 220 | 117 | h | 363 |
| 75 | D-pyrala | 256 | 119 | k | 377 |
| 28 | k | 271 | 140 | ε-Lys | 538 |
| 26 | h | 304 | 142 | δ-Orn | 563 |
| 21 | a | 467 | 158 | Thiopro | 1457 |
| 67 | Thiopro | 549 | 177 | t4-benz | 3634 |
| 80 | L-isoN | 765 | 174 | L-hmP | 6845 |
| 89 | 3-2Met | 2753 | 182 | D-Cit | NA |

Amino acids are shown in one letter codes, with lower case letters designating amino acids in the D-configuration. Other abbreviations are as shown in Table II.

The 36 peptides were screened for MC receptor binding activity in rat brain and in mouse B16 cells. The $IC_{50}$ values for some of these peptides are shown in Table VI. The peptide Ac-His-(pCl-f)-Arg-(D-Nal)-$NH_2$ (SEQ ID NO: 10), was active below 1 μM with an IC50 value of 18 nM.

TABLE Vb $IC_{50}$ values for most active mixtures from the screening data

| Library No. | XXOX | $IC_{50}$ μM | Library No. | XXXO | $IC_{50}$ μM |
|---|---|---|---|---|---|
| 197 | R | 41 | 328 | D-Nal | 107 |
| 240 | L-Cha | 59 | 307 | r | 135 |
| 209 | I | 105 | 299 | h | 209 |
| 216 | r | 142 | 322 | ε-Lys | 245 |
| 250 | pCl-F | 164 | 282 | K | 546 |
| 210 | k | 190 | 301 | k | 559 |
| 232 | α-Orn | 266 | 297 | e | NA |
| 251 | pCl-f | 648 | | | |
| 217 | s | 928 | | | |
| 265 | L-hmP | 1021 | | | |
| 256 | L-pyrala | 1216 | | | |
| 208 | h | 1847 | | | |
| 272 | Npecot | 2213 | | | |
| 229 | eAca | 3363 | | | |
| 273 | D-Cit | NA | | | |
| 249 | Thiopro | NA | | | |

Amino acids are shown in one letter codes, with lower case letters designating amino acids in the D-configuration. Other abbreviations are as shown in Table II.

TABLE VI

| Peptide | Rat-Brain $IC_{50}$ (nM) | Mouse B16 $IC_{50}$ (nM) |
|---|---|---|
| AC—H-(pcl-f)-R-(Nal)-$NH_2$ | 18 | 68 |
| Ac—H-(pCl-f)-(L-Cha)-r-$NH_2$ | >5000 | 156 |
| Ac-(αFmLys)-(pCl-f)-R-(Nal)-$NH_2$ | 427 | 41 |
| Ac-(αFmLys)-R-(L-Cha)-(Nal)-$NH_2$ | >4000 | 1143 |
| Ac-(αFmLys)-R-(L-Cha)-r-$NH_2$ | 427 | 185 |
| Ac-(αFmLys)-(D-Thi)-R-(Nal)-$NH_2$ | 469 | >4000 |
| Ac-(αFmLys)-R-R-(Nal)-$NH_2$ | 1995 | 1416 |
| Ac—H-(pCl-f)-R-(D-Nal)-$NH_2$ (SEQ ID NO:18) | 51 | 19 |

These results show that tetrapeptides that bind to MC receptors were identified from a positional scanning combinatorial library.

Although the invention has been described with reference to the examples provided above, it should be understood that various modifications can be made without departing from the spirit of the invention. Accordingly, the invention is limited only by the following claims.

We claim:

1. A peptide (SEQ ID NO:1) Ac-Nle-Gln-His-(p(I)-D-Phe)-Arg-(D-Trp)-Gly-$NH_2$.

2. A composition of matter, comprising a pharmaceutically acceptable carrier and the peptide (SEQ ID NO:1) Ac-Nle-Gln-His-(p(I)-D-Phe)-Arg-(D-Trp)-Gly-$NH_2$.

3. A radiolabeled peptide (SEQ ID NO:1) Ac-Nle-Gln-His-(p($^{125}$I)-D-Phe)-Arg-(D-Trp)-Gly-$NH_2$.

4. A melanocotin receptor bound peptide, comprising the sequence:
Nle-Gln-His-(p(I)-D-Phe)-Arg-(D-Trp)-Gly (SEQ ID NO:1), wherein said peptide binds a melanocortin receptor.

5. The peptide of claim 4, wherein said peptide is radiolabeled with $^{125}$I.

* * * * *

UNITED STATES PATENT AND TRADEMARK OFFICE
CERTIFICATE OF CORRECTION

PATENT NO. : 6,350,430 B1
DATED : February 26, 2002
INVENTOR(S) : Dooley et al.

It is certified that error appears in the above-identified patent and that said Letters Patent is hereby corrected as shown below:

Title page,
Item [73], Assignee, please delete "Lion Bioscience Science AG (DE)" and replace with -- Lion Bioscience AG (DE) --
Item [57], ABSTRACT,
Line 3, please delete "Nlc" and replace with -- Nle --
Line 4, please delete "Cly" and replace with -- Gly --

Column 2,
Line 36, please delete "HP 457" and replace with -- HP 467 --

Column 4,
Line 66, please delete "$IC_5$" and replace with -- $IC_{50}$ --

Column 12,
Line 58, please delete "(+SEM)" and replace with -- (±SEM) --

Column 13,
Line 25, please delete "$Cly-NH_2$" and replace with -- $Gly-NH_2$ --

Column 16,
Line 46, please delete "AC-H-" and replace with -- Ac-H- --
Lines 46 and 47, please delete "(pcl-f)" and replace with -- (pCl-f) --

Column 26,
Line 57, please delete "melanocotin" and replace with -- melanocortin --

Signed and Sealed this

Twenty-seventh Day of July, 2004

JON W. DUDAS
*Acting Director of the United States Patent and Trademark Office*